(12) United States Patent
Ohlemacher et al.

(10) Patent No.: US 10,280,400 B2
(45) Date of Patent: May 7, 2019

(54) METHOD FOR PRODUCING RETINAL GANGLION CELLS FROM PLURIPOTENT CELLS

(71) Applicant: Indiana University Research and Technology Corporation, Indianapolis, IN (US)

(72) Inventors: Sarah K. Ohlemacher, Indianapolis, IN (US); Jason S. Meyer, Zionsville, IN (US)

(73) Assignee: Indiana University Research and Technology Corporation, Indianapolis, IN (US)

( * ) Notice: Subject to any disclaimer, the term of this patent is extended or adjusted under 35 U.S.C. 154(b) by 138 days.

(21) Appl. No.: 15/308,796

(22) PCT Filed: May 5, 2015

(86) PCT No.: PCT/US2015/029321
§ 371 (c)(1),
(2) Date: Nov. 3, 2016

(87) PCT Pub. No.: WO2015/171663
PCT Pub. Date: Nov. 12, 2015

(65) Prior Publication Data
US 2017/0211039 A1     Jul. 27, 2017

Related U.S. Application Data

(60) Provisional application No. 61/988,775, filed on May 5, 2014.

(51) Int. Cl.
*C12N 5/0793* (2010.01)
*C12N 5/079* (2010.01)

(52) U.S. Cl.
CPC ........... *C12N 5/062* (2013.01); *C12N 5/0621* (2013.01); *C12N 2500/05* (2013.01); *C12N 2500/32* (2013.01); *C12N 2500/38* (2013.01); *C12N 2501/11* (2013.01); *C12N 2501/115* (2013.01); *C12N 2501/415* (2013.01); *C12N 2501/91* (2013.01); *C12N 2506/02* (2013.01); *C12N 2509/00* (2013.01)

(58) Field of Classification Search
CPC ................................................... C12N 5/062
See application file for complete search history.

(56) References Cited

U.S. PATENT DOCUMENTS

| 2010/0304481 A1 | 12/2010 | Thomson et al. |
| 2011/0081719 A1 | 4/2011 | Gamm et al. |
| 2011/0223140 A1* | 9/2011 | Park ..................... C12N 5/0621 424/93.7 |
| 2013/0040330 A1 | 2/2013 | Sasai et al. |

FOREIGN PATENT DOCUMENTS

| CA | 2856867 | 5/2013 |
| EP | 2700709 | 2/2014 |

OTHER PUBLICATIONS

Tucker et al. (Jan. 2014, J. Stem Cell Res. Ther., vol. 4(1), pp. 1-7). (Year: 2014).*
Brevini et al., 2010, Theriogenology, vol. 74, pp. 544-550 (Year: 2010).*
Marx V. (2013, Cell Culture Technology, vol. 496, pp. 253-258). (Year: 2013).*
Jagatha et al. (2009, Biochemical and Biophysical Res. Comm., vol. 380, pp. 230-235). (Year: 2009).*
Lamba et al. (2006, PNAS, vol. 103(34), pp. 12769-12774) (Year: 2006).*
Buta et al. (2013, Stem Cell Res., vol. 11, pp. 552-562) (Year: 2013).*
Jean et al. (2013, Develop. Growth Differ., vol. 55, pp. 41-51) (Year: 2013).*
Gomez et al. (2010, Theriogenology, vol. 74, pp. 498-515) (Year: 2010).*
Munoz et al. (2008, Theriogenology, vol. 69, pp. 1159-1164) (Year: 2008).*
Paris et al. (2010, Theriogenology, vol. 74, pp. 516-524) (Year: 2010).*
International Search Report and Written Opinion in PCT/US2015/029321 dated Jan. 11, 2016, 9 pages.
Gill et al., "Methods of Retinal ganglion Cell Differentiation From Pluripotent Stem Cells," Translational Vision Science & Technology, Jul. 1, 2014, vol. 3, No. 4, 13 pages.
Sluch et al. "Differentiation of human ESCs to retinal ganglion cells using a CRISPR engineered reported cell line," Scientific Reports, Nov. 13, 2015, vol. 5, 17 pages.
Al-Shamekh, S. and Goldberg, J.L. 2014. Retinal repair with induced pluripotent stem cells. Transl. Res. 163:377-386.
Badea, T.C. and Nathan, J. 2011. Morphologies of mouse retinal ganglion cells expressing transcription factors Brn3a, Brn3b, and Brn3c: Analysis of wild type and mutant cells using genetically-directed sparse labeling. Vision Res. 51:269-279.
Badea, T.C., Williams, J., Smallwood, P., Shi, M., Motajo, O., and Nathans, J. 2012. Combinatorial expression of Brn3 transcription in somatosensory neurons: Genetic and Morphologic and analysis. J. Neurosci. 32:995-1007.
Belecky-Adams, T., Tomarev, S., Li, H.S., Ploder, L., McInnes, R.R., Sundin, O., and Adler, R. 1997. Pax-6, Prox 1, and Chx10 homeobox gene expression correlates with phenotypic fate of retinal precursor cells. Invest. Ophthalmol. Vis. Sci. 38:1293-1303.
Bharti, K., Liu, W., Csermely, T., Bertuzzi, S., and Arnheiter, H. 2008. Alternative promoter use in eye development: The complex role and regulation of the transcription factor MITF. Development. 135:1169-1178.

(Continued)

*Primary Examiner* — Thaian N Ton
*Assistant Examiner* — David A. Montanari
(74) *Attorney, Agent, or Firm* — Faegre Baker Daniels LLP

(57) ABSTRACT

A method of making retinal ganglion cells, comprises the steps of: (a) differentiating pluripotent stem cells into retinal progenitor cells; and, (b) differentiating retinal progenitor cells into retinal ganglion cells.

11 Claims, 12 Drawing Sheets

Specification includes a Sequence Listing.

(56) References Cited

OTHER PUBLICATIONS

Bryant, J., Goodyear, R.J., and Richardson, G.P. 2002. Sensory organ development in the inner ear: Molecular and cellular mechanisms. Br. Med. Bull. 63:39-57.

Buchholz, D.E., Hikita, S.T., Rowland, T.J., Friedrich, A.M., Hinman, C.R., Johnson, L.V., and Clegg, D.O. 2009. Derivation of functional retinal pigmented epithelium from induced pluripotent stem cells. Stem Cells 27:2427-2434.

Buchholz, D.E., Pennington, B.O., Croze, R.H., Hinman, C.R., Coffey, P.J., and Clegg, D.O. 2013. Rapid and efficient directed differentiation of human pluripotent stem cells into retinal pigmented epithelium. Stem Cells Transl. Med. 2:384-393.

Capowski, E.E., Simonett, J.M., Clark, E.M., Wright, L.S., Howden, S.E., Wallace, K.A., Petelinsek, A.M., Pinilla, I., Phillips, M.J., Meyer, J.S., Schneider, B.L., Thomson, J.A., and Gamm, D.M. 2014. Loss of MITF espression during profileration. Hum. Mol. Genet. 23:6332-6344.

Carr, A.J., Vugler, A.A., Hikita, S.T., Lawrence, J.M., Gias, C., Chen, L.L., Buchholz, D.E., Ahmado, A., Semo, M., Smart, M.J., Hasan, S., da Cruz, L., Johnson, L.V., Clegg, D.O., and Coffey, P.J. 2009. Protective effects of human iPS-derived retinal pigment epithelium cell transplantation in the retinal dystrophic rat. PLoS One 4:e8152.

Chambers, S.M., Qi, Y., Mica, Y., Lee, G., Zhang, X.J., Niu, L., Bilsland, J., Cao, L., Stevens, E., Whiting, P., Shi, S.H., and Studer, L. 2012. Combined small-molecule inhibition accelerates developmental timing and converts human pluripotent stem cells into nociceptors. Nat. Biotechnol. 30:715-720.

Ferrer, M., Corneo, B., Davis, J., Wan, Q., Miyagishima, K.J., King, R Maminishkis, A., Marugan, J., Sharma, R., Shure, M., Temple, S., Miller, S., and Bharti, K. 2014. A multiplex high-throughput gene expression assay to simultaneously detect disease and functional markers in induced pluripotent stem cell-derived retinal pigment epithelium. Stem Cells Transl. Med. 3:911-922.

Fuhrmann, S., Levine, E.M., and Reh, T.A. 2000. Extraocular mesenchyme patterns the optic vesicle during early eye development in the embryonic chick. Development 127:4599-4609.

Gamm, D.M. and Meyer, J.S. 2010. Directed differentiation of human induced pluripotent stem cells: A retina perspective. Regen. Med. 5:315-317.

Gonzalez-Cordero, A., West, E.L., Pearson, R.A., Duran, Y., Carvalho, L.S., Chu, C.J., Naeem, A., Blackford, S.J., Georgiadis, A., Lakowski, J., Hubank, M., Smith, A.J., Bainbridge, J.W., Sowden, J.C., and Ali, R.R. 2013. Photoreceptor precursors derived from three-dimensional embryonic stem cell cultures integrate and mature within adult degenerate retina. Nat. Biotechnol. 31:741-747.

Hirami, Y., Osakada, F., Takahashi, K., Okita, K., Yamanaka, S., Ikeda, H., Yoshimura, N., and Takahashi, M. 2009. Generation of retinal cells from mouse and human induced pluripotent stem cells. Neurosci. Lett. 458:126-131.

Horsford, D.J., Nguyen, M.T., Sellar, G.C., Kothary, R., Arnheiter, H., and McInnes, R.R. 2005. Chx10 repression of Mitf is required for the maintenance of mammalian neuroretinal identity. Development 132:177-187.

Jin, Z.B., Okamoto, S., Osakada, F., Homma, K., Assawachananont, J., Hirami, Y., Iwata, T., and Takahashi, M. 2011. Modeling retinal degeneration using patient-specific induced pluripotent stem cells. PLoS One 6:e17084.

Jin, Z.B., Okamoto, S., Xiang, P., and Takahashi, M. 2012. Integration-free induced pluripotent stem cells derived from retinitis pigmentosa patient for disease modeling. Stem Cells Transl. Med. 1:503-509.

Lamba, D.A., Karl, M.O., Ware, C.B., and Reh, T.A. 2006. Efficient generation of retinal progenitor cells from human embryonic stem cells. Proc. Natl. Acad. Sci. U.S.A. 103:12769-12774.

Lamba, D.A., McUsic, A., Hirata, R.K., Wang, P.R., Russell, D., and Reh, T.A. 2010. Generation, purification and transplantation of photoreceptors derived from human induced pluripotent stem cells. PLoS One 5:e8763.

Liao, J.L., Yu, J., Huang, K., Hu, J., Diemer, T., Ma, Z., Dvash, T., Yang, X.J., Travis, G.H., Williams, D.S., Bok, D., and Fan, G. 2010. Molecular signature of primary retinal pigment epithelium and stem-cell-derived RPE cells. Hum. Mol. Genet. 19:4229-4238.

Livesey, F.J. and Cepko, C.L. 2001. Vertebrate neural cell-fate determination: Lessons from the retina. Nat. Rev. Neurosci. 2:109-118.

Ludwig, T.E., Bergendahl, V., Levenstein, M.E., Yu, J., Probasco, M.D., and Thomson, J.A. 2006. Feeder-independent culture of human embryonic stem cells. Nat. Methods 3:637-646.

Marquardt, T. and Gruss, P. 2002. Generating neuronal diversity in the retina: One for nearly all. Trends Neurosci. 25:32-38.

Martinez-Morales, J.R., Dolez, V., Rodrigo, I., Zaccarini, R., Leconte, L., Bovolenta, P., and Saule, S. 2003. OTX2 activates the molecular network underlying retina pigment epithelium differentiation. J. Biol. Chem. 278:21721-21731.

Maruotti, J., Wahlin, K., Gorrell, D., Bhutto, I., Lutty, G., and Zack, D.J. 2013. A simple and scalable process for the differentiation of retinal pigment epithelium from human pluripotent stem cells. Stem Cells Transl. Med. 2:341-354.

Mellough, C.B., Sernagor, E., Moreno-Gimeno, I., Steel, D.H., and Lako, M. 2012. Efficient stage-specific differentiation of human pluripotent stem cells toward retinal photoreceptor cells. Stem Cells 30:673-686.

Meyer, J.S., Shearer, R.L., Capowski, E.E., Wright, L.S., Wallace, K.A., McMillan, E.L., Zhang, S.C., and Gamm, D.M. 2009. Modeling early retinal development with human embryonic and induced pluripotent stem cells. Proc. Natl. Acad. Sci. U.S.A. 106:16698-16703.

Meyer, J.S., Howden, S.E., Wallace, K.A., Verhoeven, A.D., Wright, L.S., Capowski, E.E., Pinilla, I., Martin, J.M., Tian, S., Stewart, R., Pattnaik, B., Thomson, J.A., and Gamm, D.M. 2011. Optic vesicle-like structures derived from human pluripotent stem cells facilitate a customized approach to retinal disease treatment. Stem Cells 29:1206-1218.

Nakano, T., Ando, S., Takata, N., Kawada, M., Muguruma, K., Sekiguchi, K., Saito, K., Yonemura, S., Eiraku, M., and Sasai, Y. 2012. Self-formation of optic cups and storable stratified neural retina from human ESCs. Cell Stem Cell 10:771-785.

Oliver, G. and Gruss, P. 1997. Current views on eye development. Trends Neurosci. 20:415-421.

Osakada, F., Ikeda, H., Mandai, M., Wataya, T., Watanabe, K., Yoshimura, N., Akaike, A., Sasai, Y., and Takahashi, M. 2008. Toward the generation of rod and cone photoreceptors from mouse, monkey and human embryonic stem cells. Nat. Biotechnol. 26:215-224.

Park, I.H., Zhao, R., West, J.A., Yabuuchi, A., Huo, H., Ince, T.A., Lerou, P.H., Lensch, M.W., and Daley, G.Q. 2008. Reprogramming of human somatic cells to pluripotency with defined factors. Nature 451:141-146.

Phillips, M.J., Wallace, K.A., Dickerson, S.J., Miller, M.J., Verhoeven, A.D., Martin, J.M., Wright, L.S., Shen, W., Capowski, E.E., Percin, E.F., Perez, E.T., Zhong, X., Canto-Soler, M.V., and Gamm, D.M. 2012. Blood-derived human iPS cells generate optic vesicle-like structures with the capacity to form retinal laminae and develop synapses. Invest. Ophthalmol Vis. Sci. 53:2007-2019.

Phillips, M.J., Perez, E.T., Martin, J.M., Reshel, S.T., Wallace, K.A., Capowski, E.E., Singh, R., Wright, L.S., Clark, E.M., Barney, P.M., Stewart, R., Dickerson, S.J., Miller, M.J., Percin, E.F., Thomson, J.A., and Gamm, D.M. 2014. Modeling human retinal development with patient-specific induced pluripotent stem cells reveals multiple roles for visual system homeobox 2. Stem Cells 32:1480-1492.

Reichman, S., Terray, A., Slembrouck, A., Nanteau, C., Orieux, G., Habeler, W., Nandrot, E.F., Sahel, J.A., Monville, C., and Goureau, O. 2014. From confluent human iPS cells to self-forming neural retina and retinal pigmented epithelium. Proc. Natl. Acad. Sci. U.S.A. 111:8518-8523.

Rowan, S., Chen, C.M., Young, T.L., Fisher, D.E., and Cepko, C.L. 2004. Transdifferentiation of the retina into pigmented cells in ocular retardation mice defines a new function of the homeodomain gene Chx10. Development 131:5139-5152.

Rowland, T.J., Blaschke, A.J., Buchholz, D.E., Hikita, S.T., Johnson, L.V., and Clegg, D.O. 2013. Differentiation of human pluripotent

(56) References Cited

OTHER PUBLICATIONS stem cells to retinal pigmented epithelium in defined conditions using purified extracellular matrix proteins. J. Tissue Eng. Regen. Med. 7:642-653.

Shi, M., Kumar, S.R., Motajo, O., Kretschmer, F., Mu, X., and Badea, T.C. 2013. Genetic interactions between Brn3 transcription factors in retinal ganglion cell type specification. PLoS One 8:e76347.

Shibahara, S., Yasumoto, K., Amae, S., Udono, T., Watanabe, K., Saito, H., and Takeda, K. 2000. Regulation of pigment cell-specific gene expression by MITF. Pigment. Cell Res. 13:98-102.

Singh, R., Phillips, M.J., Kuai, D., Meyer, J., Martin, J.M., Smith, M.A., Perez, E.T., Shen, W., Wallace, K.A., Capowski, E.E., Wright, L.S., and Gamm, D.M. 2013a. Functional analysis of serially expanded human iPS cell-derived RPE cultures. Invest Ophthalmol. Vis. Sci. 54:6767-6778.

Singh, R., Shen, W., Kuai, D., Martin, J.M., Guo, X., Smith, M.A., Perez, E.T., Phillips, M.J., Simonett, J.M., Wallace, K.A., Verhoeven, A.D., Capowski, E.E., Zhang, X., Yin, Y., Halbach, P.J., Fishman, G.A., Wright, L.S., Pattnaik, B.R., and Gamm, D.M. 2013b. iPS cell modeling of Best disease: Insights into the pathophysiology of an inherited macular degeneration. Hum. Mol. Genet. 22:593-607.

Sridhar, A., Steward, M.M., and Meyer, J.S. 2013. Nonxenogeneic growth and retinal differentiation of human induced pluripotent stem cells. Stem Cells Transl. Med. 2:255-264.

Stern, J. and Temple, S. 2014. Stem cells for retinal repair. Dev. Ophthalmol. 53:70-80.

Takahashi, K., Tanabe, K., Ohnuki, M., Narita, M., Ichisaka, T., Tomoda, K., and Yamanaka, S. 2007. Induction of pluripotent stem cells from adult human fibroblasts by defined factors. Cell 131:861-872.

Thomson, J.A., Itskovitz-Eldor, J., Shapiro, S.S., Waknitz, M.A., Swiergiel, J.J., Marshall, V.S., and Jones, J.M. 1998. Embryonic stem cell lines derived from human blastocysts. Science 282:1145-1147.

Tucker, B.A., Anfinson, K.R., Mullins, R.F., Stone, E.M., and Young, M.J. 2013a. Use of a synthetic xeno-free culture substrate for induced pluripotent stem cell induction and retinal differentiation. Stem Cells Transl. Med. 2:16-24.

Tucker, B.A., Mullins, R.F., Streb, L.M., Anfinson, K., Eyestone, M.E., Kaalberg, E., Riker, M.J., Drack, A.V., Braun, T.A., and Stone, E.M. 2013b. Patient-specific iPSC-derived photoreceptor precursor cells as a means to investigate retinitis pigmentosa. Elife. (Cambridge) 2:e00824.

Vugler, A., Can, A.J., Lawrence, J., Chen, L.L., Burrell, K., Wright, A., Lundh, P., Semo, M., Ahmado, A., Gias, C., da Cruz, L., Moore, H., Andrews, P., Walsh, J., and Coffey, P. 2008. Elucidating the phenomenon of HESC-derived RPE: Anatomy of cell genesis, expansion and retinal transplantation. Exp. Neurol. 214:347-361.

Wahlin, K.J., Maruotti, J., and Zack, D.J. 2014. Modeling retinal dystrophies using patient-derived induced pluripotent stem cells. Adv. Exp. Med. Biol. 801:157-164.

Weir, J., Rivolta, M., and Holley, M. 2000. Identification of differentiating cochlear hair cells in vitro. Am. J. Otol. 21:130-134.

Wright, L.S., Phillips, M.J., Pinilla, I., Hei, D., and Gamm, D.M. 2014. Induced pluripotent stem cells as custom therapeutics for retinal repair: Progress and rationale. Exp. Eye. Res. 123:161-172.

Yu, J., Vodyanik, M.A., Smuga-Otto, K., AntosieWicz-Bourget, J., Frane, J.L., Tian, S., Nie, J., Jonsdottir, G.A., Ruotti, V., Stewart, R., Slukvin, II, and Thomson, J.A. 2007. Induced pluripotent stem cell lines derived from human somatic cells. Science 318:1917-1920.

Zhang, S.S., Fu, X.Y., and Barnstable, C.J. 2002. Molecular aspects of vertebrate retinal development. Mol. Neurobiol. 26:137-152.

Zhong, X., Gutierrez, C., Xue, T., Hampton, C., Vergara, M.N., Cao, L.H., Peters, A., Park, T.S., Zambidis, E.T., Meyer, J.S., Gamm, D.M., Yau, K.W., and Canto-Soler, M.V. 2014. Generation of three-dimensional retinal tissue with funtional photoreceptors from human iPSCs. Nat. Commun. 5:4047.

\* cited by examiner

METHOD FOR PRODUCING RETINAL GANGLION CELLS FROM PLURIPOTENT CELLS

CROSS REFERENCE TO PRIOR APPLICATIONS

This application is a U.S. National Phase filing of PCT/US2015/029321, filed May 5, 2015, which claims the benefit of U.S. Provisional Patent Application No. 61/988,775, filed May 5, 2014, the entire disclosures of both which are hereby expressly incorporated by reference herein.

STATEMENT OF GOVERNMENTAL RIGHTS

This invention was made with government support under EY027984 awarded by National Institutes of Health. The government has certain rights in the invention.

FIELD OF THE DESCRIPTION

The present description relates generally to methods of preparing cells from pluripotent stem cells. More particularly, the description relates to methods of preparing retinal ganglion cells from pluripotent stem cells, and more specifically human pluripotent stem cells.

BACKGROUND OF THE DESCRIPTION

Human pluripotent stem cells, which include both human embryonic stem cells (hESCs) and human induced pluripotent stem cells (hiPSCs), hold the potential to differentiate into any cell type. As such, they can serve as comprehensive model systems of human cell genesis, particularly at early developmental stages that would otherwise be inaccessible to investigation. In addition, patient-derived hiPSC lines have a unique capacity to model human disease, although the scope of disorders amenable to this form of study is limited. Major considerations when creating hiPSC disease models include the capacity to efficiently generate, identify and isolate relevant cell populations, as well as recapitulate and assay critical aspects of the disease mechanism.

Retinal cell types are particularly well-suited for the investigation of cell development and dysfunction using pluripotent stem cell technology. The vertebrate retina harbors a modest repertoire of major cell classes sequentially produced via a conserved series of events. Furthermore, the effects of inherited and acquired retinal degenerative diseases (RDD) are often limited initially to a specific cell class, which simplifies the study of cellular mechanisms that incite RDD and the evaluation of potential therapies.

Previous studies have demonstrated the ability of human pluripotent stem cells to differentiate along the retinal lineage with varying efficiencies, with one protocol achieving a near uniform retinal cell fate using the WA01 hESC line (Lamba et al., 2011). However, pluripotent stem cell-derived retinal cells, particularly those from hiPSCs, are most often found in mixed populations that include some non-retinal or unidentified cell types. Further complicating matters is the fact that several markers used for retinal cell identification (e.g., calretinin, PKCα, Tuj1) also label cells found in other regions of the CNS. As such, a means to isolate developmentally synchronized populations of multipotent retinal progenitor cells (RPCs) across multiple hESC and hiPSC lines would be desirable. The RPCs and their definitive retinal progeny could then be used to study mechanisms of human retinal development and disease, examine retinal cell function, and devise and test RDD treatments.

In recent years, several groups have described the ability to direct human pluripotent stem cells (hPSCs) to a retinal fate (Lamba et al., 2006, 2010; Osakada et al., 2008; Carr et al., 2009; Hirami et al., 2009; Nakano et al., 2012; Buchholz et al., 2013). In order to serve as an effective in vitro model for human retinogenesis, as well as provide a foundation for translational applications, the stepwise differentiation of hPSCs through all of the major stages of retinogenesis helps to ensure the proper differentiation and prospective identification of hPSC-derived retinal progeny (Meyer et al., 2009, 2011; Gamm and Meyer, 2010; Sridhar et al., 2013).

The present inventors have previously described a method to differentiate human pluripotent stem cells to RPCs, retinal pigment epithelium (RPE), and photoreceptor-like cells in a manner that mimicked normal human retinogenesis (Meyer et al., 2009; the entire contents of which are incorporated herein by reference). However, a means to separate and track the fate of the RPCs in live culture was not available at that time. The present inventors have also described a method wherein transient morphological features were used to isolate structures with characteristics reminiscent of the optic vesicle (OV) (Meyer et al., 2011; the entire contents of which are incorporated herein by reference). Using such OV-like structures, it was possible to study principles of early human retinal development, monitor the sequence and timing of neuroretinal cell genesis, and optimize RPC and RPE production efficiencies in recalcitrant hiPSC lines.

SUMMARY OF THE DESCRIPTION

In one aspect, the present description provides a method of making retinal ganglion cells, comprises the steps of: (a) differentiating pluripotent stem cells into retinal progenitor cells; and, (b) differentiating retinal progenitor cells into retinal ganglion cells.

In another aspect, the present description provides a method of making retinal ganglion cells, comprising the steps of:

(a) differentiating human pluripotent stem cells into retinal progenitor cells, the retinal progenitor cells expressing one or more of Chx10 and Pax6 and lacking Sox1 expression; and (b) differentiating retinal progenitor cells into retinal ganglion cells, the retinal ganglion cells having one or more of:
  retinal ganglion cell morphology;
  ability to fire action potentials;
  ability to exhibit inward sodium currents that are sensitive to a voltage-gated sodium channel blocker;
  ability to conduct potassium through voltage-gated channels; and
  Brn3 expression.

In another aspect, the present description provides a method of preparing retinal ganglion cells from human pluripotent stem cells or human induced pluripotent cells. In one aspect, the pluripotent cells are derived from glaucoma patients.

In another aspect, the present description provides a novel method of preparing retinal ganglion cells from pluripotent stem cells including the step of inhibiting Wnt.

BRIEF DESCRIPTION OF THE FIGURES

The features of certain embodiments of the invention will become more apparent in the following detailed description in which reference is made to the appended figures.

DESCRIPTION OF THE PREFERRED EMBODIMENTS

The method and protocols outlined herein are used to differentiate human pluripotent stem cells (hPSCs) into retinal cell types through a process that faithfully recapitulates the stepwise progression observed in vivo. From pluripotency, cells are differentiated to a primitive anterior neural fate, followed by progression into two distinct populations of retinal progenitors and forebrain progenitors, each of which can be manually separated and purified. The hPSC-derived retinal progenitors are found to self-organize into three-dimensional optic vesicle-like structures, with each aggregate possessing the ability to differentiate into all major retinal cell types. The ability to faithfully recapitulate the stepwise in vivo development in a three-dimensional cell culture system allows for the study of mechanisms underlying human retinogenesis. Furthermore, this methodology allows for the study of retinal dysfunction and disease modeling using patient-derived cells, as well as high-throughput pharmacological screening and eventually patient-specific therapies.

Figure 1:
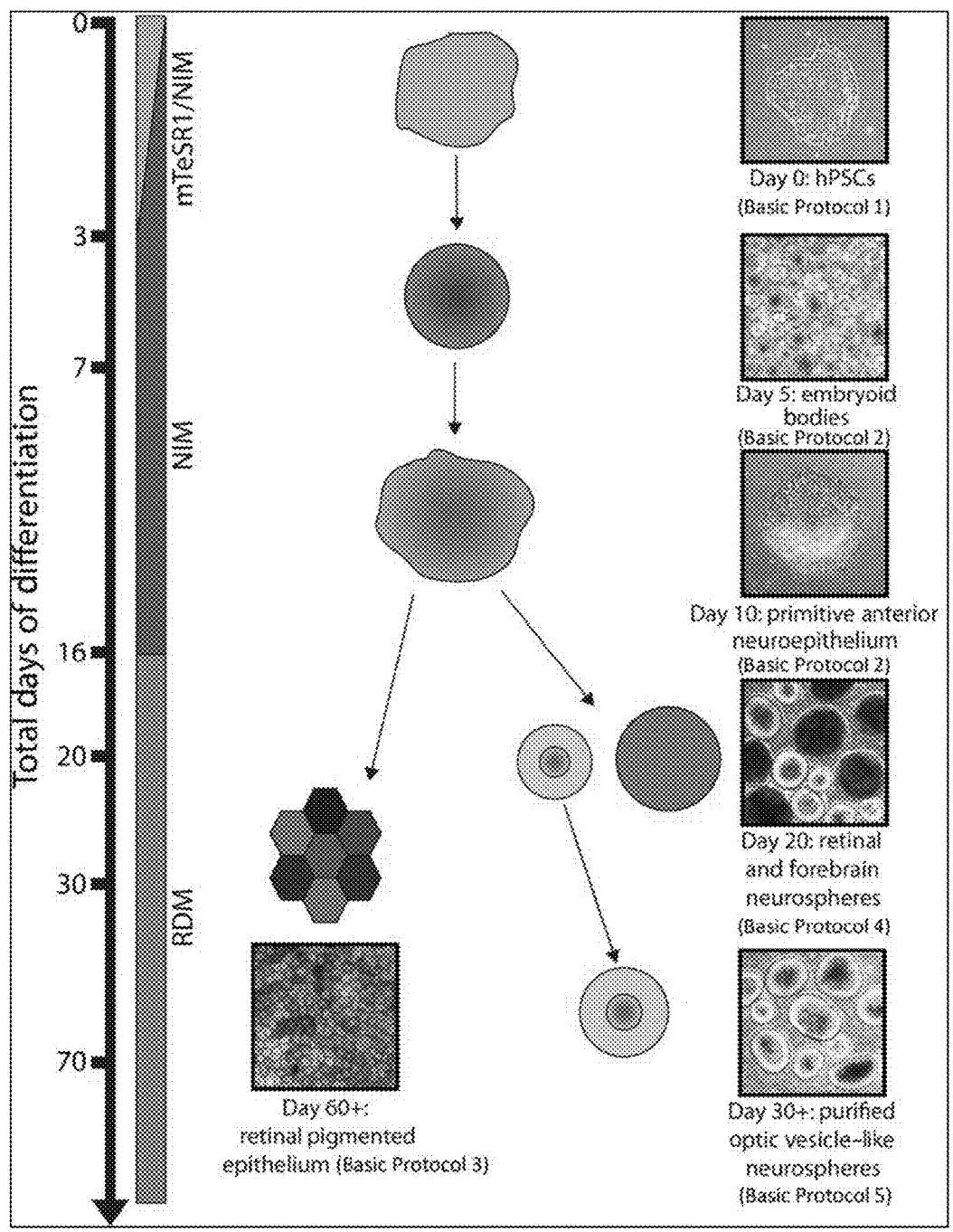
FIG. 1: Overview of retinal differentiation protocol. hPSCs can be directed to differentiate into all retinal cell types in a stepwise process. First, undifferentiated hPSCs are directed to differentiate by the generation of embryoid bodies. By 7 total days of differentiation, embryoid bodies are plated as adherent cultures. By 16 total days, neurospheres are generated, and by 20 total days, retinal progenitor populations may be enriched. The maintained cultures of retinal neurospheres will yield all major cell types of the neural retina within the first 70 days of differentiation. Alternatively, optic vesicle-like cultures at day 16 of differentiation may be utilized to generate retinal pigment epithelium through the maintenance of adherent cultures.

As described herein, and as illustrated in FIG. 1, there is provided a procedure to efficiently differentiate retinal cells from hPSCs. As shown, cells are taken through a stepwise protocol to direct them toward a neural fate by treatment with neural induction medium (NIM), then to a retinal fate by exposure to retinal differentiation medium (RDM). First, undifferentiated hPSCs are enzymatically lifted from Matrigel-coated plates (see Basic Protocol 1) and exposed to NIM in suspension (see Basic Protocol 2). Differentiation in suspension allows the cells to form three-dimensional aggregates. At 7 days of differentiation, aggregates are plated and attached to 6 well plates, where a neuroepithelial fate is established (see Basic Protocol 2). At 16 days of differentiation, the neuroepithelial cells can be induced to a retinal pigment epithelial (RPE) fate by culturing with heparin and growth factors (see Basic Protocol 3). Alternatively, neurospheres can be lifted and maintained in RDM to establish a three-dimensional optic vesicle-like fate (see Basic Protocol 4). This procedure allows for the efficient and timely generation of a variety of retinal cell types (see Basic Protocol 5), including ganglion cells and cone and rod photoreceptors. The use of this protocol to generate a myriad of retinal cell types facilitates in vitro studies of human retinogenesis (Meyer et al., 2009, 2011; Zhong et al., 2014)), and provides a large population of cells for use in studies of retinal dysfunction (e.g. Meyer et al., 2011, Jin et al., 2012; Singh et al., 2013; Wahlin et al., 2014; Wright et al., 2014) as well as drug development and patient-specific therapies (Carr et al., 2009; Lamba et al., 2010; Al-Shamekh and Goldberg, 2014; Stern and Temple, 2014).

EXAMPLES

The following protocols are provided by way of example only. It will be understood that although some specific steps/reagents etc. are recited in the description of the following protocols, such specifics are intended only to illustrate certain aspects of the invention and are not intended to limit the scope of the invention in any way. Various modifications to the protocols will be apparent to persons skilled in the art and in view of the common general knowledge within the scope of the claims appended hereto.

Generally, the protocols described below should be performed in a Class II biological culture hood to prevent contamination of cells. The standard incubation temperature is 37° C. with 5% CO2. As will be understood by persons skilled in the art, all medium and solutions added directly to cells must be warm. It is recommended that reagents be heated in a 37° C. water bath prior to use.

Basic Protocol 1: Enzymatic Passaging of hPSCs

Figure 2:
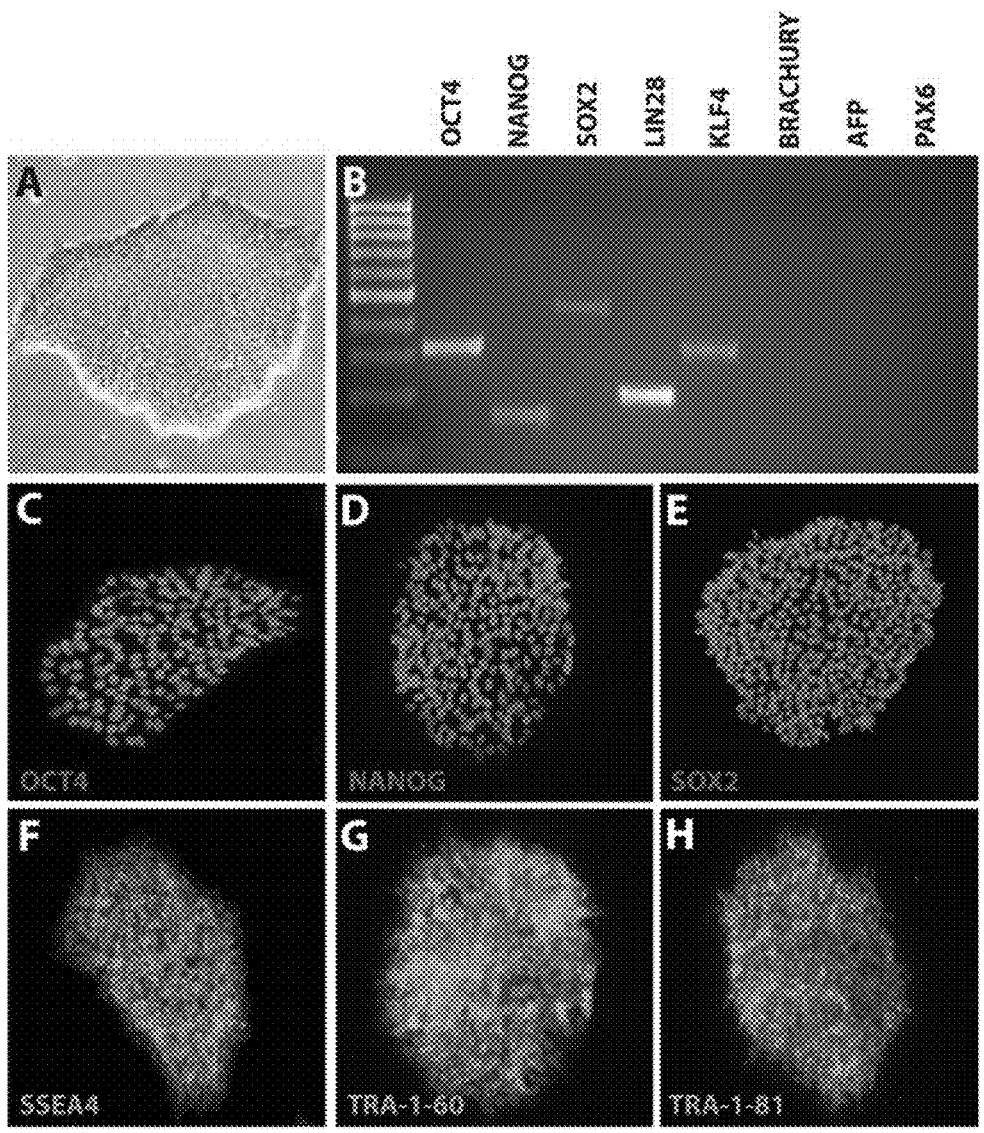
FIG. 2: Characterization of undifferentiated hPSCs. (A) hPSCs display a typical undifferentiated morphology, including tightly packed colonies of cells and clearly defined edges. (B) RT-PCR analysis demonstrates presence of characteristic pluripotency markers in hPSCs and a lack of mesodermal, endodermal, and ectodermal markers. (C-H) Immunocytochemistry demonstrates widespread expression of pluripotency-associated transcription factors (red) and cell surface markers (green).

The following procedure is used to maintain and passage hPSCs for long-term use (Thomson et al., 1998; Ludwig et al., 2006; Takahashi et al., 2007; Yu et al., 2007; Park et al., 2008; Meyer et al., 2009, 2011; Sridhar et al., 2013) and to harvest hPSCs for subsequent differentiation. It focuses on the use of mTeSR1 medium and Matrigel to maintain hPSCs, although previous reports have demonstrated the ability to maintain hPSCs in alternate systems such as fibroblast feeder cells (Meyer et al., 2009, 2011; Sridhar et al., 2013). Cells are maintained on Matrigel-coated six-well culture plates and are split when confluency reaches ~70%. This will aid in preventing spontaneous differentiation of cells due to overgrowth, while ensuring that an abundant amount of cells can be collected for directed differentiation. Typically, hPSCs are expanded at a ratio of 1:6, with a single well of cells capable of seeding an entire six-well plate. The starting population of hPSCs should display a tightly clustered and bright morphology and exhibit immunoreactivity to pluripotency markers (FIG. 2). A list of primers and antibodies suitable for RT-PCR and immunocytochemistry are provided in Tables 1 and 2.

Materials
  hPSCs growing on Matrigel™-coated six-well plate 2
    mg/ml dispase solution (see recipe) DMEM/F12, 1:1
    (Life Technologies)
  mTeSR™1 (Stemcell Technologies)
  Inverted light microscope 15-ml conical tubes
  Matrigel™-coated six-well plate (see recipe)
  Passage Undifferentiated Cells
    1) Place a six-well plate of hPSCs under an inverted light microscope and mark areas of spontaneous differentiation.
    2) Transfer plate to a biological safety cabinet and use a 1-ml pipet tip to scrape away any cells from the marked areas of differentiation.
    3) Aspirate medium from wells and replace with 1 ml/well of 2 mg/ml dispase solution. Transfer to incubator for 10 min and monitor every few minutes to ensure cells are beginning to detach from the culture surface. If dispase is sufficiently warmed to 37° C., this process should not take more than 15 min.
    4) Once a majority of cell clusters display curled edges, immediately remove dispase by aspiration.
    5) Wash cells once with 1 ml DMEM/F12 per well, adding the medium to the side of the well, not directly onto the cells, so that colonies are not prematurely detached from the surface.
    6) Aspirate DMEM/F12 and add another 1 ml DMEM/F12 per well, this time with force directly onto the cells to detach the colonies. Repeat several times, if needed. It is better to forcefully dislodge colonies by pipetting three or four times than to gently agitate any more than this. Minimizing the amount the cells are broken up is key to ensuring maximum survival.

7) Transfer cells from wells that will be expanded to one 15-ml conical tube and cells from wells for retinal differentiation to another 15-ml conical tube. Proceed to step 8 for expansion or to Basic Protocol 2 for differentiation.

Expand Undifferentiated hPSCs

8) Allow cells to settle to the bottom of the tube by gravity or by centrifuging 1 min at 100×g. Aspirate supernatant, taking care not to disturb the cell pellet.

9) Resuspend cells in mTeSR™1 medium so that each new well will receive 500 µl suspension (i.e., to passage one well of hPSCs to six new wells, use 3 ml mTeSR1). Break up clusters by pipetting forcefully four to five times with a 5 ml serological pipet to give clusters that are ~100 to 150 µm in diameter. Note that cell lines can vary in ease of breaking up cell clusters. If clusters are not broken up sufficiently, increase pipetting during the next passage. It is better that clusters remain large than to be broken up too much.

10) Pipet 500 µl undifferentiated cell suspension at a 90° angle into each well of a freshly prepared Matrigel™-coated six-well plate.

11) Transfer to the incubator and agitate plates in side-to-side followed by front-to-back motions to ensure even distribution of cells. Be sure to pause briefly between series of agitations to ensure that cells are evenly dispersed across the well rather than accumulated in the middle.

Change medium daily (2 ml/well) until the next passage, typically within 4 to 5 days.

Figure 3:
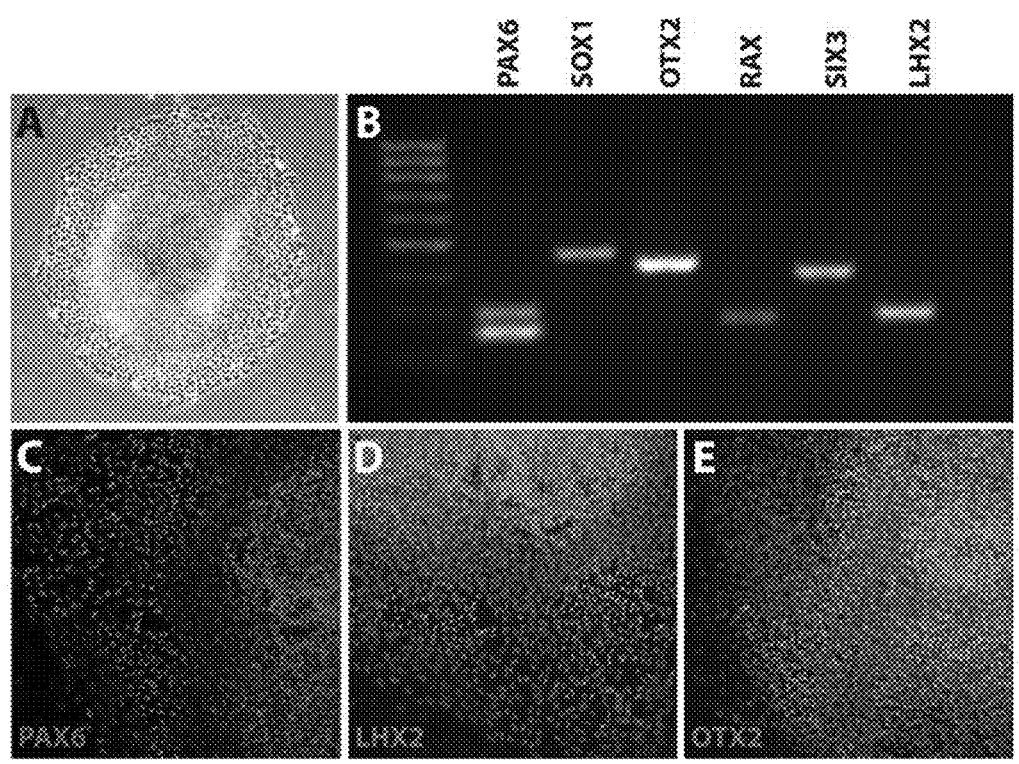
FIG. 3: Induction of hPSCs to a neural progenitor fate. hPSCs were analyzed after 10 days of differentiation and plating. (A) At 10 days, colonies appear more three-dimensional in the center, becoming more flattened and enlarged toward the periphery. (B) RT-PCR analysis demonstrates expression of neural markers PAX6 and SOX1. An anterior neural eye-field fate was further indicated by expression of OTX2, RAX, SIX3, and LHX2. (C-E) Immunocytochemistry demonstrates widespread expression of many of these transcription factors.

Basic Protocol 2: Induction of hPSCs to a Primitive Anterior Neuroepithelial Fate As retinal cells are derived from a pluripotent source through a stepwise process in vivo (Oliver and Gruss, 1997; Livesey and Cepko, 2001; Marquardt and Gruss, 2002; Zhang et al., 2002), hPSCs should be differentiated through analogous stages of differentiation, including a primitive anterior neural fate, an optic vesicle stage, and eventually a retinal and/or RPE fate (Meyer et al., 2009, 2011; Sridhar et al., 2013; Zhong et al., 2014). To initiate this stepwise process, embryoid bodies (EBs) are kept in suspension to begin differentiation for the first 7 days. This phase requires a slow transition out of mTeSR™1 medium into NIM and maintenance in a T75 flask. After 7 total days of differentiation, EBs are plated onto six-well culture plates to allow for further neural differentiation. This can be accomplished by addition of 10% FBS for the first 24 hr of plating to ensure that cells adhere to the wells. EBs are maintained in NIM until day 16. By day 10, they can be characterized by a larger, more uniform appearance as well as the expression of typical neural and eye-field transcription factors (FIG. 3).

Materials
Harvested and washed undifferentiated hPSCs (see Basic Protocol 1, steps 1-8) mTeSR1 (Stemcell Technologies)
Neural induction medium (NIM; see recipe)
Fetal bovine serum (FBS)
T75 culture flask (Falcon)
15-ml conical tube
Six-well culture plate
Generate Embryoid Bodies 1. Day 0: Allow cells to settle to the bottom of the tube by gravity. Aspirate supernatant and gently resuspend pellet in a 3:1 mixture of mTeSR™1/NIM. Transfer to a T75 flask and place in the incubator overnight. Day 0 is defined as the day cells are lifted from the Matrigel™-coated plate.

2. Day 1: Transition cells to a 1:1 mixture of mTeSR™1/NIM as described in step 1.

3. Day 2: Transition cells to a 1:3 mixture of mTeSR™1/NIM as described in step 1.

4. Day 3: Transition cells to complete NIM as described in step 1. Continue culturing until day 7, replacing medium with fresh NIM every other day.

5. Day 7: Collect EBs in a 15-ml conical tube and allow them to settle by gravity, typically within 5 min.

6. Add 2 ml NIM to each well of an uncoated six-well plate. In general, EBs derived from five wells of undifferentiated cells will plate on one six-well plate, with ~30 to 40 EBs per well.

7. Aspirate supernatant from the EBs, being careful not to disturb the cell pellet. Resuspend EBs in NIM so that each well will receive 200 µl suspension (e.g., 1.2 ml NIM for one plate), and add cells to the six-well plate accordingly.

8. Add 250 µl of FBS to each well (final concentration, ~10%) to promote cell attachment.

9. Place in the incubator overnight, agitating in a side-to-side and then front-to-back manner to ensure an even distribution of cells within each well.

10. Day 8: Aspirate medium and add 2 ml fresh NIM without FBS to each well.

11. Return to incubator and change medium every other day until day 16 of differentiation. At this point, cells will have acquired a primitive anterior neuroepithelial fate.

Figure 4:
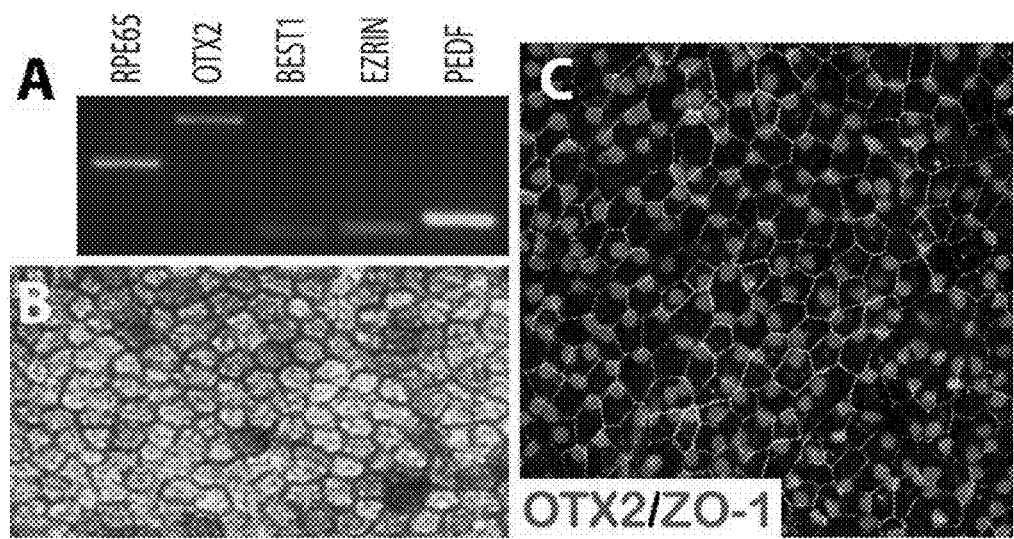
FIG. 4: Differentiation of hPSCs to retinal pigment epithelium (RPE). (A) hPSC-derived RPE-like cells express typical RPE-associated markers when screened by RT-PCR. (B) Under bright-field microscopy, they display proper morphological features distinct to RPE, including hexagonal shape and areas of pigmentation. (C) Immunocytochemical analysis reveals features typical of the RPE, including expression of tight junction proteins such as ZO-1 and transcription factors such as OTX2.

Basic Protocol 3: Differentiation of Primitive Anterior Neuroepithelial Cells to a Retinal Pigment Epithelial Fate During normal development, the RPE is the first retinal cell type to be specified from a more primitive source. The RPE layer develops in a manner that is distinctly separate from the neural retinal populations of cells, and is known to be specified in the absence of factors instrumental in directing a neural retinal fate (Fuhrmann et al., 2000; Shibahara et al., 2000; Martinez-Morales et al., 2003). Likewise, RPE cells generated from hPSCs are found to differentiate through a similar process in which RPE cells are often found in close proximity to, although distinctly separate from, neural retinal populations (Capowski et al., 2014; Zhong et al., 2014). hPSC-derived primitive anterior neuroepithelial cells on six-well plates can be used to generate a highly purified population of RPE. These hPSC-derived RPE cells can be readily identified by their accumulation of pigmentation and their distinct hexagonal morphology (FIG. 4), and have been successfully generated by many groups in recent years (Vugler et al., 2008; Buchholz et al., 2009, 2013; Carr et al., 2009; Meyer et al., 2009, 2011; Liao et al., 2010; Maruotti et al., 2013; Rowland et al., 2013; Singh et al., 2013a; Sridhar et al., 2013; Capowski et al., 2014; Ferrer et al., 2014).

Materials
Primitive anterior neuroepithelial cells in six-well plate (see Basic Protocol 2) Retinal differentiation medium (RDM; see recipe)
Epidermal growth factor (EGF) Fibroblast growth factor 2 (FGF2) Heparin
Inverted light microscope
Tungsten needle, pipet tip, or other pointed object
Laminin/polyornithine-coated coverslips in a 4- or 24-well plate (see Support Protocol)

1) Day 16 of differentiation: Change medium from NIM to RDM and return to incubator. Continue culturing and changing medium every 2 to 3 days until distinct populations of RPE cells are readily observed and can be isolated (typically within 60 total days of differentiation).

2) Day of RPE isolation: Using a microscope, identify a suitably pure area of RPE based on pigmentation and hexagonal "cobblestone-like" morphology.

3) Using a pointed object (e.g., tungsten needle, pipet tip), gently scratch away an area around the region of cells to be microdissected, freeing the RPE cells.

4) Using a P100 pipettor, transfer the freed cluster of RPE cells in 50 µl RDM to a laminin/polyornithine-coated coverslip in a 4- or 24-well plate. Typically, one cluster of RPE cells should be sufficient for one coverslip.

5) Repeat this process for as many coverslips as needed.

6) Transfer the plate to the incubator and allow RPE to attach overnight. After overnight incubation, RPE clusters should have adhered to the coverslips.

7) Add 500 µl RDM supplemented with 20 ng/ml EGF, 20 ng/ml FGF2, and 2 µg/ml heparin to allow for proliferation of RPE cells. Continue culturing and replacing medium and growth factors every 2 days. RPE cells are expected to double in number approximately every 36 hr. Within 7 to 10 days, RPE cells will have lost most of their pigmentation and hexagonal shape, and will have occupied most of the coverslip.

8) To allow for maturation and reacquisition of RPE morphology, replace RDM containing growth factors with RDM alone and maintain for 2 to 3 weeks, or until a desired stage of RPE maturation is reached. RPE differentiated in this fashion may be maintained for at least two weeks.

Basic Protocol 4: Differentiation and Long-Term Maintenance of Retinal Progenitor Cells During in vivo development, after cells have adopted a primitive anterior neural phenotype, a subset of cells are known to acquire a retinal fate beginning with the optical vesicle stage of retinogenesis, and are characterized by numerous retinal-associated features that distinguish these cells from other neural lineages (Belecky-Adams et al., 1997; Rowan et al., 2004; Horsford et al., 2005; Bharti et al., 2008). Once this optic vesicle identity has been established, all mature retinal cell types (cones, rods, retinal ganglion cells, and so on) will eventually arise. Likewise, hPSCs can progress through an optic vesicle-like intermediary (FIG. 5), eventually yielding all of the major cell types of the retina (Meyer et al., 2009, 2011; Sridhar et al., 2013; Capowski et al., 2014; Phillips et al., 2014). To accomplish this, cells are lifted from the culture surface at 16 days of differentiation and maintained in floating suspension in RDM to allow for development of a three-dimensional optic vesicle-like structure. Retinal and non-retinal cells can then be manually separated and maintained until the desired stage of differentiation is reached.

Materials

Primitive anterior neuroepithelial cells in six-well plate (see Basic Protocol 2) Retinal differentiation medium (RDM; see recipe)

60×15 mm polystyrene Petri dishes

Six-well plates (Falcon)

Generate Neurospheres from Primitive Anterior Neuroepithelial Cells

1) Day 16 of differentiation: Using a P1000 pipettor, draw up 1 ml medium from a well of cells and dislodge the center of each aggregate from the plate by vigorously pipetting the medium directly at the center of the aggregate. Repeat several times, if needed, to dislodge the center and leave a ring of peripheral cells possessing a flattened appearance. It is better to pipet forcefully five to six times instead of gently pipetting any more than this, as excessive pipetting results in cell death and reduced yield of neurospheres.

2) Transfer dislodged aggregates to a 15-ml conical tube and allow to settle by gravity or by centrifugation for 1 min at 100×g.

3) Aspirate supernatant and resuspend cells in 5 ml RDM.

Figure 5:
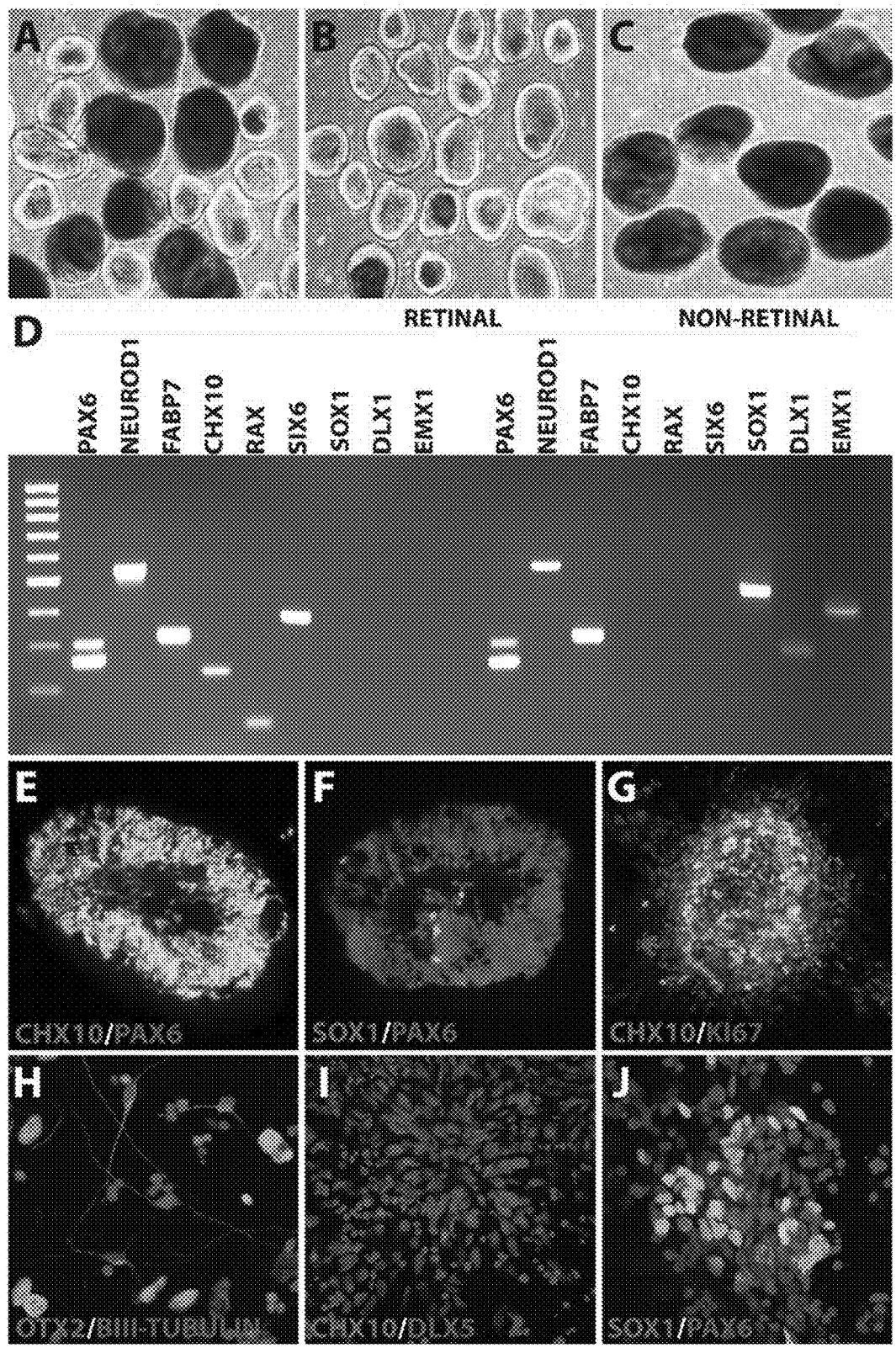
FIG. 5: Identification, enrichment, and characterization of retinal progenitor cells. (A) After 30 days of differentiation, hPSCs were isolated into two morphologically distinct and readily identifiable populations. (B) Retinal neurospheres are characterized by a bright ring surrounding the outer layer. (C) The non-retinal neural population displays a larger, more uniform appearance. (D) RT-PCR analysis reveals striking differences between populations. Whereas neural-associated transcription factors (PAX6, NeuroD1, and FABP7) are present in both populations, markers that are characteristic of retinal progenitors (CHX10, RAX, and SIX6) are present in retinal neurospheres and absent from non-retinal neural populations. Conversely, forebrain-associated transcription factors (SOX1, DLX1, and EMX1) are expressed in non-retinal neural cells and absent from retinal neurospheres. (E-J) Immunocytochemical analysis reveals that retinal neurospheres widely express the retinal progenitor markers CHX10 and PAX6 (E), but largely lack expression of the forebrain-associated marker SOX1 (F). hPSC-derived retinal progenitors also remain highly proliferative within the first 30 days of differentiation (G). Non-retinal neural populations display typical features of emerging forebrain neurons, including expression of βIII tubulin and OTX2 (H) and forebrain-associated DLX5 (I), but lack the retinal progenitor marker CHX10 (I). Non-retinal neural cells also retain expression of both PAX6 and SOX1 (J).

4) Transfer cell suspension to a 60-mm dish and return to the incubator. Continue culturing for up to 25 total days of differentiation, changing medium every 2 to 3 days. By 20 to 25 total days of differentiation, two populations of neurospheres will begin to emerge: retinal neurospheres that have a golden ring around the outside, and non-retinal forebrain neurospheres that have a darker appearance and lack this golden ring. These morphological differences can easily be observed with an inverted microscope under a 4× objective. By 30 total days of differentiation, distinct transcriptional profiles emerge that distinguish these two populations (FIG. 5). Enrichment of retinal neurospheres should be performed by day 25 of differentiation.

Manually Enrich Retinal Neurospheres

5) While viewing the cells under an inverted light microscope with a 4× objective, swirl the plate gently in a circular motion to collect cells in the middle of the dish.

6) Looking at the neurospheres through the microscope, gently gather retinal neurospheres based on their bright outer ring appearance using a P20 pipettor and transfer them to a 15 ml conical tube containing 5 ml RDM. Repeat until all retinal neurospheres have been collected in the same tube.

7) Transfer retinal neurospheres (along with the medium) to a 60-mm dish and return to the incubator. Non-retinal neurospheres may be similarly maintained for neuronal cultures, if desired, or discarded at this stage.

Maintain Retinal Neurospheres

8) Culture retinal neurospheres until the desired stage of retinal differentiation is reached, changing the medium every other day as follows:

a. Tilt the plate towards you to allow the medium and neurospheres to collect in the bottom half of the plate.

b. While maintaining the tilt of the plate, use a P1000 pipettor to transfer 1 ml medium containing as many neurospheres as possible to a 15 ml conical tube.

c. Collect the remaining medium and rinse over the entire surface of the plate to collect any remaining neurospheres. Transfer this remaining medium to the 15-ml conical tube.

d. Allow neurospheres to settle to the bottom of the tube, then aspirate the supernatant.

e. Resuspend neurospheres in 5 ml fresh RDM and transfer back to the dish. Retinal ganglion cells are expected to arise after 40 total days of differentiation, and photoreceptor progenitor cells are expected to arise within 70 total days of differentiation.

Basic Protocol 5: Induction of Retinal Progenitors to Specific Retinal Subtypes

Figure 6:
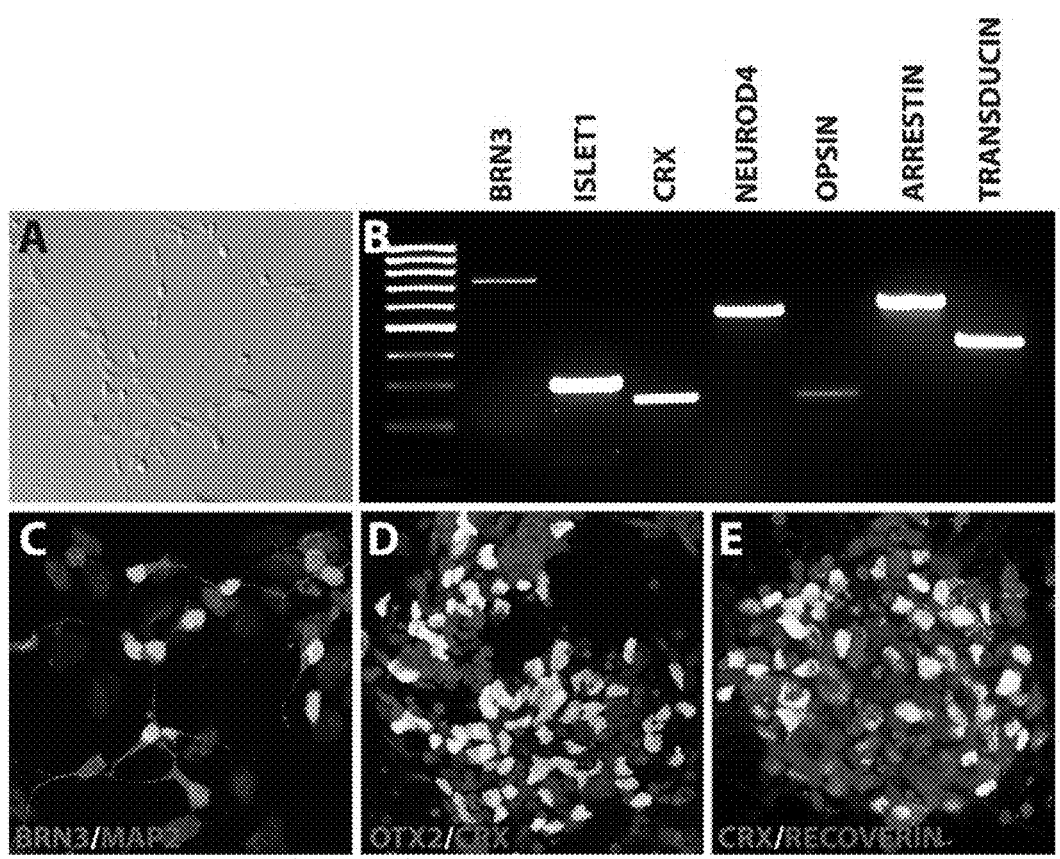
FIG. 6: Differentiation of hPSCs to retinal neurons. (A) Within 90 total days of differentiation, hPSC-derived retinal cells display typical neuronal morphologies under DIC microscopy. (B) Analysis by RT-PCR illustrates an array of retinal-associated transcription factors, including those associated with ganglion cells (BRN3 and Islet1) and photoreceptors (CRX and NeuroD4). Proteins associated with phototransduction (Red/Green Opsin, Arrestin, and Transducin) are also expressed. (C-E) Immunocytochemistry confirms expression of BRN3-positive retinal ganglion cells extending Map2-positive dendrites, as well as photoreceptor-like phenotypes, including expression of CRX, OTX2, and Recoverin.

Previous studies have demonstrated that hPSC-derived retinal progenitor cells have the ability to yield all major classes of retinal cells, including photoreceptors (Lamba et al., 2006, 2010; Osakada et al., 2008; Meyer et al., 2009, 2011; Mellough et al., 2012; Gonzalez-Cordero et al., 2013; Tucker et al., 2013a, 2013b; Reichman et al., 2014; Zhong et al., 2014) and retinal ganglion cells (Lamba et al., 2010; Meyer et al., 2011; Sridhar et al., 2013; Zhong et al., 2014). In order to derive these various cell types, retinal neurospheres must be maintained in differentiating cultures for extended periods of time. Within 90 days of total differentiation, neural retinal cell types including photoreceptors and retinal ganglion cells can be identified (FIG. 6). In order to analyze cells by immunocytochemistry, neurospheres should be dissociated with ACCUTASE (a cell detachment solution of proteolytic & collagenolytic enzymes) and then plated onto laminin/polyornithine-coated coverslips. At this point, cells demonstrate the presence of a wide variety of retinal-specific transcription factors and distinct neuroretinal morphologies, such as neurite outgrowth and/or axonal and dendritic arborization typical of retinal ganglion cell or photoreceptor morphologies (FIG. 6).

Materials

Retinal neurospheres at 40 days total differentiation (see Basic Protocol 4)

ACCUTASE (a cell detachment solution of proteolytic & collagenolytic enzymes; BD Biosciences)

Retinal differentiation medium (RDM; see recipe)

Laminin/polyornithine-coated coverslips (see Support Protocol)

Inverted light microscope 1.5 ml tube

1) Place the plate of retinal neurospheres in suspension under a microscope and swirl in a circular motion to gather cells towards the center of the field of view.

2) Gather neurospheres that will be used for dissociation and plating and transfer to a 1.5 ml tube. Two to three neurospheres per coverslip typically provide enough density for sufficient plating and microscopy.

3) Allow neurospheres to settle to the bottom of the tube and gently remove excess medium with a pipet.

4) Add 200 µl ACCUTASE (a cell detachment solution of proteolytic & collagenoloytic enzymes) and transfer to a 37° C. water bath.

5) Every 10 min, remove tube from water bath and forcefully agitate cells about four or five times with a P100 pipettor (on 50 µl setting) to break up the cells.

6) Repeat step 5, if needed, until aggregates are the desired size (ideally, ~200 to 400 µm in diameter). Viability is greatly increased if cells are dissociated to yield small aggregates of cells rather than a single-cell suspension.

7) Centrifuge suspension for 1 min at 100×g. Gently remove supernatant with a pipet.

8) Resuspend cells in enough RDM to ensure that each coverslip receives 50 µl suspension.

9) Pipet 50 µl suspension onto each laminin/polyornithine-coated coverslip.

10) Transfer to incubator and allow cells to adhere overnight.

11) If cells are to be maintained on coverslips for further differentiation, add 500 µl RDM the following day and every other day thereafter until the desired stage of differentiation is reached. If cells are to be fixed immediately for immunocytochemistry, no additional medium should be added.

Support Protocol: Coverslips with Laminin and Poly-D-Ornithine

This brief protocol explains how to coat coverslips for use in Basic Protocols 3 and 5. Poly-D-ornithine increases adhesion of cells to the coverslip, and laminin promotes cell growth. Cells grown on laminin/polyornithine-coated coverslips can easily be utilized for immunocytochemical analysis and readily transferred to slides for visualization by microscopy.

Materials 12-mm glass coverslips, washed with ethanol and subsequently autoclaved 4- and/or 24-well plates 100 µg/ml poly-D-ornithine solution (see recipe)

20 µg/ml laminin solution (see recipe)

1) Transfer one coverslip to each well of a 4- or 24-well plate and ensure that it lies flat on the bottom of the well.

2) Pipet 100 µl poly-D-ornithine onto the center of each coverslip. Let sit at room temperature for 30 min, ensuring the poly-D-ornithine remains on the coverslip.

3) Remove solution and wash each well with 1 ml sterile water. Repeat two more times.

4) Remove the third wash and check coverslips under a microscope to make sure any precipitate has been washed away. Continue rinsing if any residue remains.

5) Remove last wash and allow coverslips to air dry in a biological safety cabinet overnight. Be sure to leave the hood fan on and the sash slightly open.

6) Remove dry coverslips from hood. If desired, polyornithine-coated coverslips can be stored at room temperature for at least 1 month.

7) Add 50 µl of 20 µg/ml laminin directly to the center of each poly-D-ornithine-coated coverslip.

8) Transfer plates to the incubator and let stand at least 4 hr or overnight to allow thorough coating of coverslips.

9) Aspirate excess laminin just before addition of cell suspension. Laminin is not expected to have a long half-life, and thus laminin-coated slides should be used shortly after preparation.

Reagents and Solutions

All solutions should be made in a biological safety cabinet and filtered through a Steriflip™ or bottle top filter to ensure solutions are sterile Dispase Solution, 2 mg/ml Dissolve 2 mg/ml dispase powder (Life Technologies) completely in DMEM/F12 (1:1, Life Technologies). Warm for at least 20 min in a 37° C. water bath, then filter sterilize. Store up to 2 weeks at 4° C.

Laminin Solution, 20 µg/ml

Starting with a 1 mg/ml stock, dilute laminin 1:50 in cold DMEM to a final concentration of 20 µg/ml. Store up to 1 month at 4° C.

Matrigel-coated Plates

Dilute Matrigel (hESC-qualified, BD Biosciences) according to manufacturer's specifications in DMEM. Coat six-well culture plates (e.g., Falcon) by adding 1 ml Matrigel per well and placing in a 37° C., 5% CO2 incubator for at least 1 hr. Aspirate excess Matrigel from plates, then add 2 ml mTeSR1 medium (Stemcell Technologies) to each well. Keep at 37° C. and use within 8 hr.

Neural Induction Medium (NIM)

489.5 ml DMEM/F12 (1:1, Life Technologies)

5 ml N2 supplement (Life Technologies)

5 ml MEM non-essential amino acids 0.5 ml 2 mg/ml heparin

Filter sterilize

Store up to 1 month at 4° C.

Poly-D-Ornithine Solution, 100 µg/ml

Tap a 10-mg bottle of poly-D-ornithine (Sigma) on the surface of the hood and open carefully as to not lose any powder. Slowly pipet 1 ml sterile water into the bottle, replace the cap, and shake vigorously. Carefully remove cap and transfer solution to an autoclaved 250-ml beaker. Repeat this process about four more times to remove all traces of poly-D-ornithine from the bottle. Then, add sterile water to the beaker to bring the volume to 100 ml. Pipet up and down to mix thoroughly. Transfer aliquots to 50-ml conical tubes. Filter sterilize each aliquot using a Steriflip™ 0.2-µm filtering device. Store up to 6 months at 4° C.

Retinal Differentiation Medium (RDM)
240 ml DMEM/F12 (1:1, Life Technologies)
240 ml DMEM (Life Technologies)
10 ml B27 supplement without vitamin A (Life Technologies)
5 ml MEM non-essential amino acids
5 ml antibiotics
Filter sterilize
Store up to 1 month at 4° C.

Critical Parameters and Troubleshooting

A general troubleshooting guide is provided in Table 3. In addition, some important procedural notes are made below.

When passaging hPSCs, it is crucial to minimize the amount of pipetting, as even a little excessive pipetting can dramatically decrease the yield of EBs. Cells that have been treated with dispase should lift off the plate with little effort. Once the harvested cells have been collected into their respective tubes (for expansion or differentiation), they should be allowed to settle completely at the bottom of the tube (at least 5 min) to ensure that no cells are aspirated with the supernatant.

When plating EBs with 10% FBS, the plating density is critical to ensure proper differentiation into neuroepithelium. Without close proximity to neighboring cells, cell survival decreases. On the other hand, cells that are plated at too high a density lack the space they require to develop properly. In addition, it is important to agitate plates in the incubator to help achieve a uniform distribution of cells within the well.

Manually separating the retinal neurospheres by day 25 is critical to ensure that morphology can be definitively used to separate retinal and non-retinal cells. After day 25, retinal morphology may begin to disappear as the neurospheres continue proliferating.

When changing medium of retinal neurospheres maintained in suspension, unnecessary cell loss can be avoided by rinsing the well or dish with extra medium. This ensures all cells are collected and receive fresh medium in a timely manner.

Anticipated Results

This procedure yields a 90% pure population of CHX10-positive retinal progenitor cells that can be further differentiated into every retinal cell type.

Time Considerations

With practice, passaging of hPSCs can take as little as 20 min, once the necessary supplies and reagents have been prepared. Plating of EBs should take ~10 min for three plates. Manually separating retinal neurospheres from a mixed population can take anywhere from 30 to 60 min, depending on the yield of neurospheres and the experience of the researcher. Using ACCUTASE (a cell detachment solution of proteolytic & collagenolytic enzymes) to disassociate neurospheres can take anywhere from 10 to 40 min, depending on neurosphere size and the desired degree of disassociation.

Discussion

Human pluripotent stem cells (hPSCs) possess the unique ability to readily differentiate into any cell type of the body. As such, they can serve as comprehensive and novel tools for drug screening, disease modeling, and cell replacement therapies. Although previous studies have demonstrated the ability to differentiate hPSCs to a retinal lineage, the ability to derive retinal ganglion cells (RGCs) from hPSCs has been largely overlooked to date. In the current study, hPSCs were directed to differentiate toward a retinal ganglion cell lineage, and the developmental timing and characteristics of these cells were observed. hPSC-derived RGCs expressed a full complement of RGC associated features and possessed proper physiological characteristics. These results served as the basis for the establishment of patient-specific lines of human induced pluripotent stem cells from a glaucoma patient. Fibroblasts derived from a patient with an E50K mutation in the Optineurin (OPTN) gene were genetically reprogrammed to yield lines of patient-specific induced pluripotent stem cells through mRNA-based reprogramming strategies. These cells were then directed to differentiate toward a RGC-like fate, upon which these cells progressed through a retinal progenitor intermediary before yielding BRN3-positive retinal ganglion-like cells.

As shown in FIG. 6, after approximately 10 to 12 weeks of differentiation, PCR analysis illustrated a variety of retinal specific transcription factors, including markers associated with retinal ganglion cells and photoreceptors. Immunocytochemistry confirmed the expression of Crx, Otx2, and Recoverin within photoreceptor-like cells, as well as Brn3/Map2-positive retinal ganglion-like cells.

Figure 7:
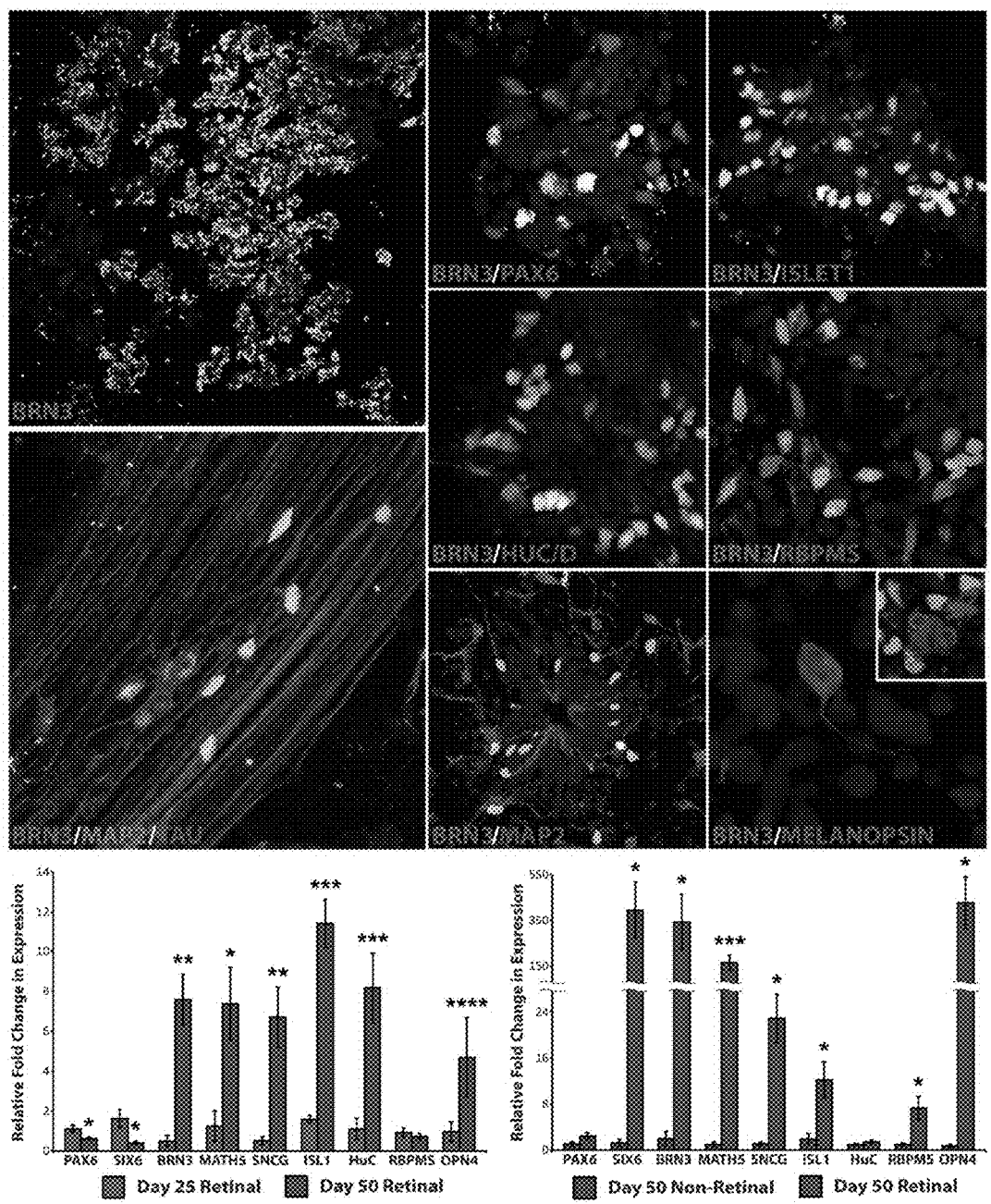
FIG. 7: IPS RGC characterization. Low magnification confocal imaging demonstrated an efficiency of approximately 35% of retinal progenitor cells acquiring RGC-associated characteristics. BRN3-positive cells displayed co-expression with the RGC-associated markers PAX6, ISLET1, HUC/D, and RBPMS. MAP2-positive neurite outgrowths appeared from BRN3-positive cells within neural rosette-like structures and eventually gave rise to elaborate RGC-like morphologies expressing MAP2 and TAU, including bundled TAU-positive axons. Moreover, a subset of intrinsically photosensitive melanopsin-positive RGCs were observed in small quantities. qRT-PCR analysis revealed significantly increased expression of RGC-associated transcripts as cells transitioned from a progenitor fate (day 25) to a retinal lineage (day 50). Additionally, enriched populations of retinal neurospheres expressed higher levels of RGC-associated genes as compared to their forebrain, non-retinal counterparts.
Figure 8:
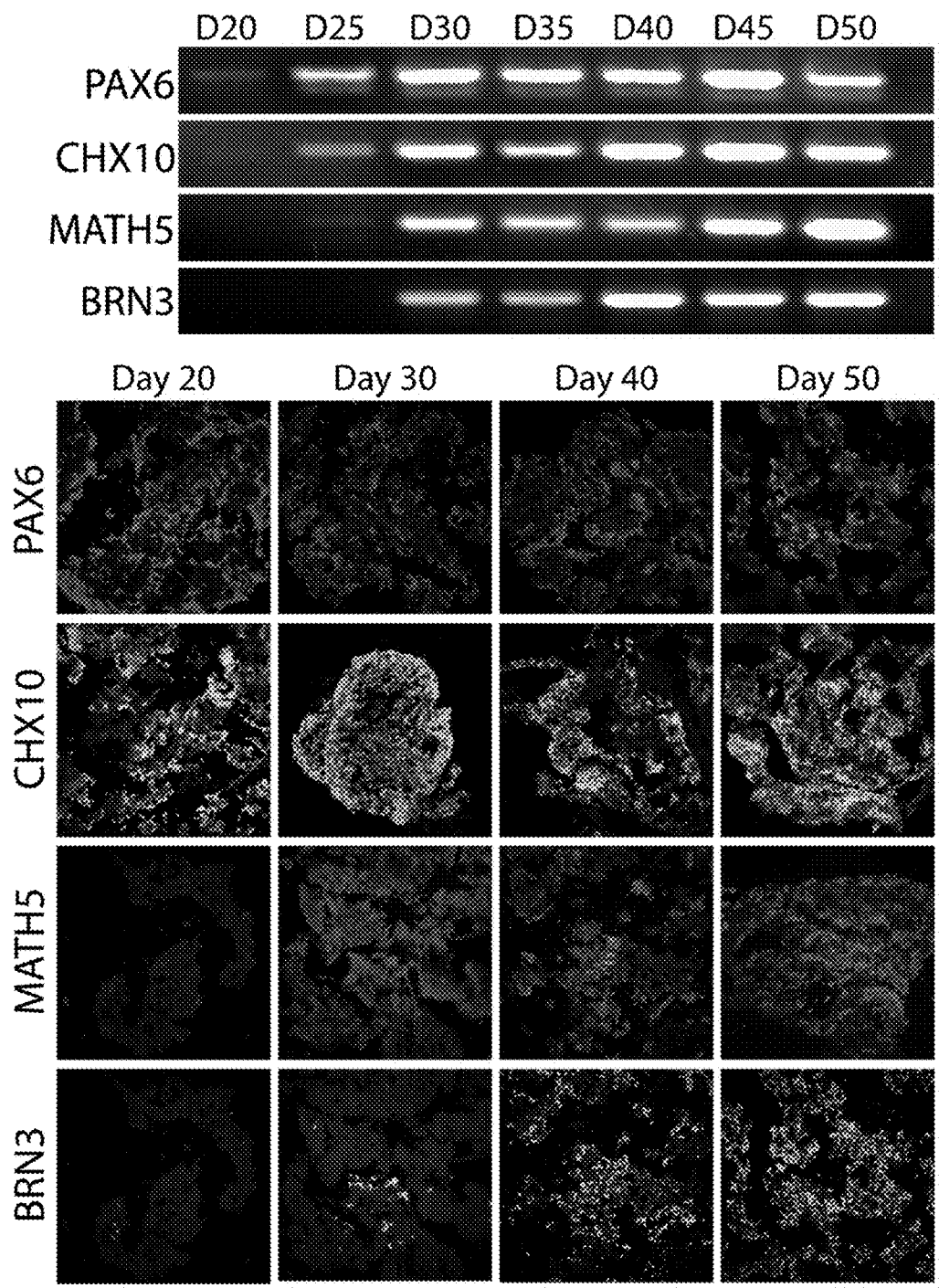
FIG. 8: RGC Developmental Timing. Transcription factors involved in specifying RGC fate showed a temporal and stepwise expression pattern. Pax6 and Chx10 expression was predictably observed in the cells from days 20 to 50, indicating a widespread progenitor population. MATH5, a transcription factor required for RGC development, showed higher expression immediately before the commitment of these cells to a BRN3 expressing RGC-like fate.
Figure 9:
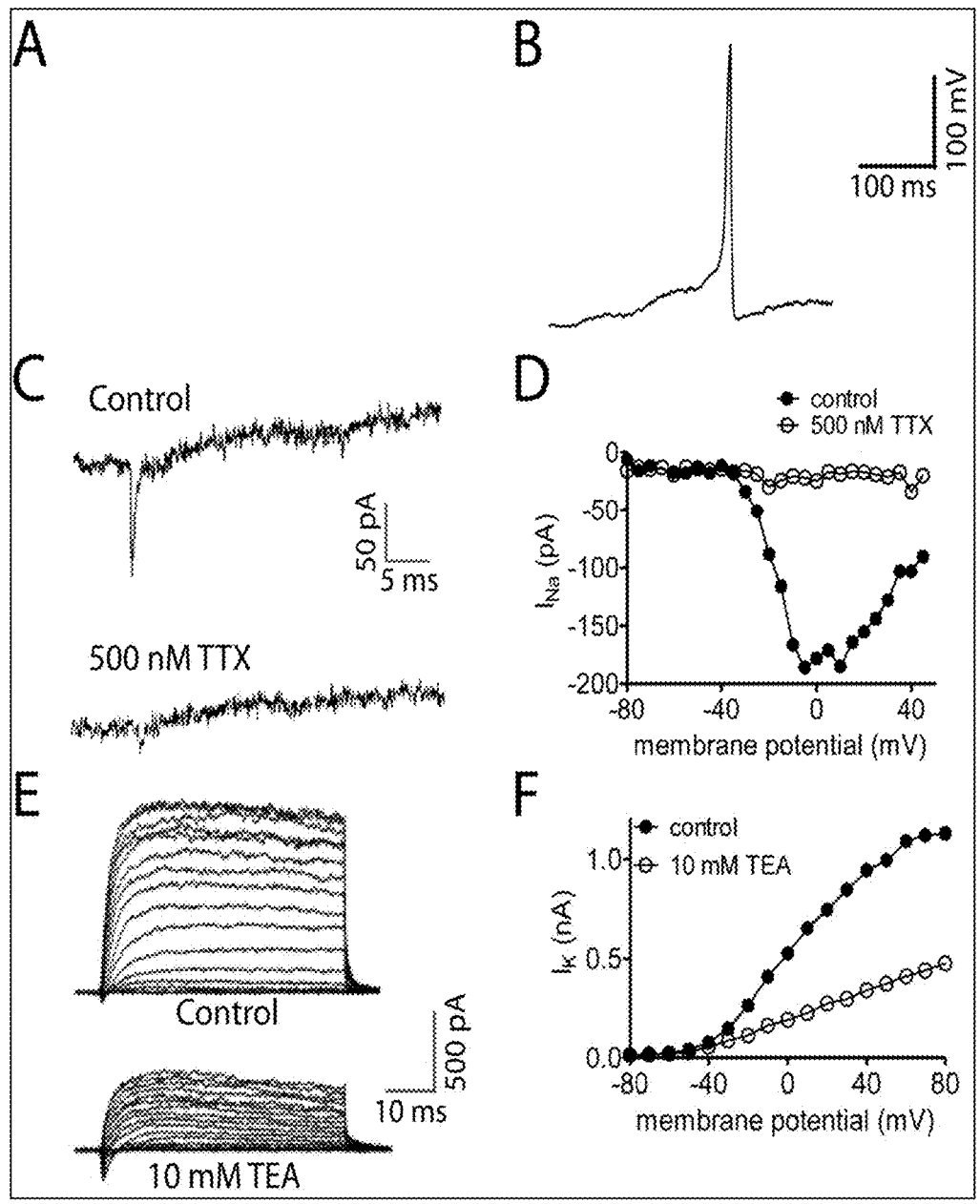
FIG. 9: RGC Physiology. Characteristic retinal ganglion cell morphologies were highlighted by differential interference contrast microscopy, including long neurite outgrowth typical of such neurons. Cells also demonstrated the ability to fire action potentials, and exhibited inward sodium currents that were sensitive to the voltage-gated sodium channel blocker, TTX. In addition, these cells exhibited conductance of potassium through voltage-gated channels.

As shown in FIG. 7, differentiation into a RGC-like fate was demonstrated by the combinatorial expression of RGC markers including Brn3, Math5, and Islet1. RGC-like cells did not co-express γ-synuclein, contrary to recent reports, or CRX, an early photoreceptor marker. Brn3/Map2 outgrowths appeared from neural rosette-like structures and eventually gave rise to elaborate RGC-like morphologies expressing Map2 and Tau. Interestingly, fasciculating Tau-positive axons were observed, associated with BRN3-positive cells. As discussed above, low magnification confocal imaging demonstrated an efficiency of approximately 35% of retinal progenitor cells acquiring RGC-associated characteristics. BRN3-positive cells displayed co-expression with the RGC-associated markers PAX6, ISLET1, HUC/D, and RBPMS. MAP2-positive neurite outgrowths appeared from BRN3-positive cells within neural rosette-like structures and eventually gave rise to elaborate RGC-like morphologies expressing MAP2 and TAU, including bundled TAU-positive axons. Moreover, a subset of intrinsically photosensitive melanopsin-positive RGCs were observed in small quantities. qRT-PCR analysis revealed significantly increased expression of RGC-associated transcripts as cells transitioned from a progenitor fate (day 25) to a retinal lineage (day 50). Additionally, enriched populations of retinal neurospheres expressed higher levels of RGC-associated genes as compared to their forebrain, non-retinal counterparts.

Thus, the present disclosure serves to establish a method by which to acquire RGCs from hPSCs. This protocol provides a novel system to study human retinogenesis, and also establishes a foundation for the development of patient specific therapies for diseases affecting retinal ganglion cells, such as glaucoma and other optic neuropathies. The disclosure also shows that hPSCs can be readily differentiated into RGC-like cells, exhibiting the proper immunoreactivity, morphology, and physiological characteristics. The disclosure also illustrates the ability to derive RGCs from hPSCs, which serves as a novel method by which to study the development of these cells in vitro. The disclosure also shows that patient specific fibroblasts with an E50K mutation in the OPTN gene can be reprogrammed to pluripotency and then directed to generate RGC-like cells. The disclosure also shows that OPTN iPSCs can serve as a novel system to study glaucoma in vitro and elucidate the mechanisms underlying the loss of RGCs as well as provide a large population of cells for drug screening and transplantation purposes.

The ability to direct the differentiation of hPSCs to a retinal fate represents a limitless source of retinal cells for in vitro studies of human retinogenesis, as well as a unique and exciting tool with which to study retinal disease progression, screen compounds for potential therapeutic efficacy, and even provide a source of replacement cells for transplantation purposes. For these reasons, several groups have explored the ability to differentiate hPSCs to a retinal fate (Lamba et al., 2006; Osakada et al., 2008; Buchholz et al., 2009; Carr et al., 2009; Hirami et al., 2009; Meyer et al., 2009, 2011; Liao et al., 2010; Mellough et al., 2012; Nakano et al., 2012; Maruotti et al., 2013; Sridhar et al., 2013; Zhong et al., 2014), with a traditional focus on differentiation of photoreceptors and RPE cells due to the availability of unique and specific characteristics with which to identify them.

The protocol described here is significant for its ability not only to differentiate retinal cells starting from a pluripotent stem cell population, but also to faithfully identify and enrich for cells at all of the major stages of retinal development (Meyer et al., 2009, 2011; Sridhar et al., 2013). Starting from an undifferentiated population of hPSCs, cells are efficiently differentiated to a primitive anterior neuroepithelial fate in high purity after as little as 10 days (FIG. 2). From this point, differentiating cells yield neurosphere populations representing either forebrain progenitor cells or optic vesicle-like retinal progenitor cells, the latter of which exclusively gives rise to more mature retinal phenotypes, including photoreceptor cells and retinal ganglion cells (Meyer et al., 2011; Sridhar et al., 2013). The ability to readily identify cells at each of these major stages is unique to the method outlined here, and helps to establish hPSCs as a valuable in vitro model of human retinogenesis.

When working with a pluripotent stem cell population, the definitive and conclusive identification of a particular differentiated cell type is often difficult. Many markers traditionally utilized to identify differentiated cell types, including those used to identify specific retinal cell types, are often expressed in other areas of the body. Thus, when working with a pluripotent cell population that has the potential to give rise to any cell type of the body, the simple expression of many of these cell type-associated markers may not be sufficient to definitively identify a differentiated cell as a particular cell type. Retinal ganglion cells represent such a cell type that would ordinarily be difficult to conclusively identify from pluripotent stem cells, as there are no markers that identify retinal ganglion cells and are not expressed elsewhere in the nervous system.

The ability to morphologically identify and isolate retinal progenitor neurospheres within the first 20 to 25 days of differentiation (FIG. 5) is noteworthy for a variety of reasons. First, the use of morphological cues to identify and isolate retinal progenitor neurospheres represents a novel method for enriching retinal cells apart from other cellular lineages, effectively yielding highly enriched populations of retinal progenitor cells that can readily differentiate into all major retinal cell types (Meyer et al., 2011; Zhong et al., 2014). This ability to highly enrich for retinal progenitor cells allows for more definitive identification of greater numbers of mature retinal cell types, including retinal ganglion cells. Within the retina itself, retinal ganglion cells are often identified by expression of the transcription factor BRN3 (Bryant et al., 2002; Badea and Nathans, 2011; Shi et al., 2013). However, BRN3 is also expressed in other neural cell types, including some auditory neurons (Weir et al., 2000; Bryant et al., 2002) as well as many somatosensory neurons (Badea et al., 2012; Chambers et al., 2012). Thus, when starting with a pluripotent stem cell source that has the potential to give rise to any cell type of the body, expression of BRN3 by itself is not sufficient to definitively identify retinal ganglion cells. With the ability to enrich for retinal progenitor cells derived from hPSCs, traditional markers such as BRN3 can be utilized to identify these retinal cells, because other non-retinal cell types will have been effectively eliminated from the culture system.

Due to the ease of differentiation and the minimal culture conditions required, this procedure allows for application of hPSCs as a novel model for in vitro studies of human retinogenesis (Meyer et al., 2009, 2011; Sridhar et al., 2013; Capowski et al., 2014; Phillips et al., 2014; Zhong et al., 2014). The ability to identify each of the major stages of retinal development has led to the recent use of this method for studying the molecular basis of cell fate determination between cells of the neural retina and the retinal pigment epithelium (Capowski et al., 2014; Phillips et al., 2014). This is significant not only due to the ability to study these events in human cells, but because these cell fate determination events are known to occur at developmental stages that are otherwise inaccessible to experimental investigation. Furthermore, recent studies have demonstrated the ability to expand upon this method to generate three-dimensional stratified retinal-like structures in vitro (Phillips et al., 2012; Zhong et al., 2014), allowing for the possibility of future studies of both cell fate determination and maturation of these cells.

This method can also be applied to the study of human inherited diseases of the retina, particularly those leading to blindness, such as age-related macular degeneration, retinitis pigmentosa, and optic neuropathies including glaucoma, among others. Using the enrichment method presented for retinal progenitor cells, large numbers of retinal cells can be readily obtained from patient-derived induced pluripotent stem cells. This approach has been utilized to effectively generate in vitro models for a variety of blinding disorders, including gyrate atrophy and Best disease (Meyer et al., 2011; Singh et al., 2013b), and offers the potential for studies of numerous other retinal degenerative disorders. In addition, the potential exists to employ this method for pharmacological screening of novel compounds for therapeutic efficacy using patient-derived cells. This was originally described in disorders affecting the RPE (Meyer et al., 2011; Singh et al., 2013b), and has been expanded to disorders affecting other retinal cell types such as photoreceptors (Jin et al., 2011). It is expected that hPSCs will provide an effective complement to traditional model systems, and will add to current methods used to study human samples, typically from post-mortem tissue or from readily accessible cell sources that are often unaffected by disease processes, particularly in the case of the retina. Thus, it is believed that hPSCs bridge an important gap for both basic and translational research between traditional model systems and the existing human condition.

Retinal ganglion cells are among the first retinal cell types specified, arising from a multipotent pool of retinal progenitor cells. As part of the development of the six major classes of cells of the neural retina, these retinal progenitor cells must be specified by both extrinsic and intrinsic cues to adopt characteristics of the different cell types of the retina. From the committed state of definitive neural progenitor cells, all of the mature cells of the nervous system have been specified, including those of the retina. Initially, after only 20 days of differentiation from hiPSCs, it is possible to identify populations of cells of the early retinal lineage, based on markers associated with the optic vesicle stage of development. Interestingly, these optic vesicle-stage cells were segregated into distinct neurosphere cultures, where greater than 90% of all cells express characteristics of the optic vesicle. On the other hand, other neurospheres within the same cultures were completely devoid of retinal cells. Using the method of differentiation discussed herein, it is possible to identify and manually isolate these neurospheres, yielding a highly enriched population of definitive retinal progenitor cells derived from hiPSCs.

The Chx10-positive retinal progenitor phase is maintained for several more weeks of differentiation. However, upon further differentiation of these cells, more mature retinal phenotypes are observed, including photoreceptors, RGCs, and retinal pigment epithelium. It is important to note that these results demonstrate that RGCs can indeed be readily generated from hiPSCs, and these previous studies were among the first descriptions of RGCs derived from human pluripotent stem cells. Furthermore, with the knowledge that these cells arose from a more primitive, Chx10-positive retinal progenitor pool, it is possible to identify these cells definitively as RGCs. As the markers typically used to identify RGCs are often expressed elsewhere in the nervous system, this earlier enrichment of retinal progenitor cells is essential when dealing with an original pluripotent cell source. However, the factors that specify an RGC fate from a more primitive retinal progenitor cell population remain largely unknown, particularly within the human system. Thus, while we have already demonstrated the ability to derive RGCs from hiPSCs, the goals of the first aim are to elucidate the mechanisms by which an RGC fate arises from these hiPSC-derived retinal progenitor cells and thus, generate a more efficient method by which to derive RGCs from an hiPSC source.

Glaucoma is a devastating degenerative disease of the retina that primarily affects the retinal ganglion cells (RGCs), leading to their degeneration and subsequent loss of vision. While systems exist with which to study glaucoma-related damage to RGCs, the ability to study such a phenotype in a human system has been largely limited. A human in vitro model for studying glaucoma-related symptoms could better elucidate underlying mechanisms of the disease, including both cell autonomous and non-cell autonomous effects, and potentially offer new therapeutic options for patients with glaucoma. Derived from human somatic cells, human induced pluripotent stem cells (hiPSCs) are generated through the genetic reprogramming of these cells that are able to differentiate into any cell type of the body, making them uniquely suited for such studies.

Figure 10:
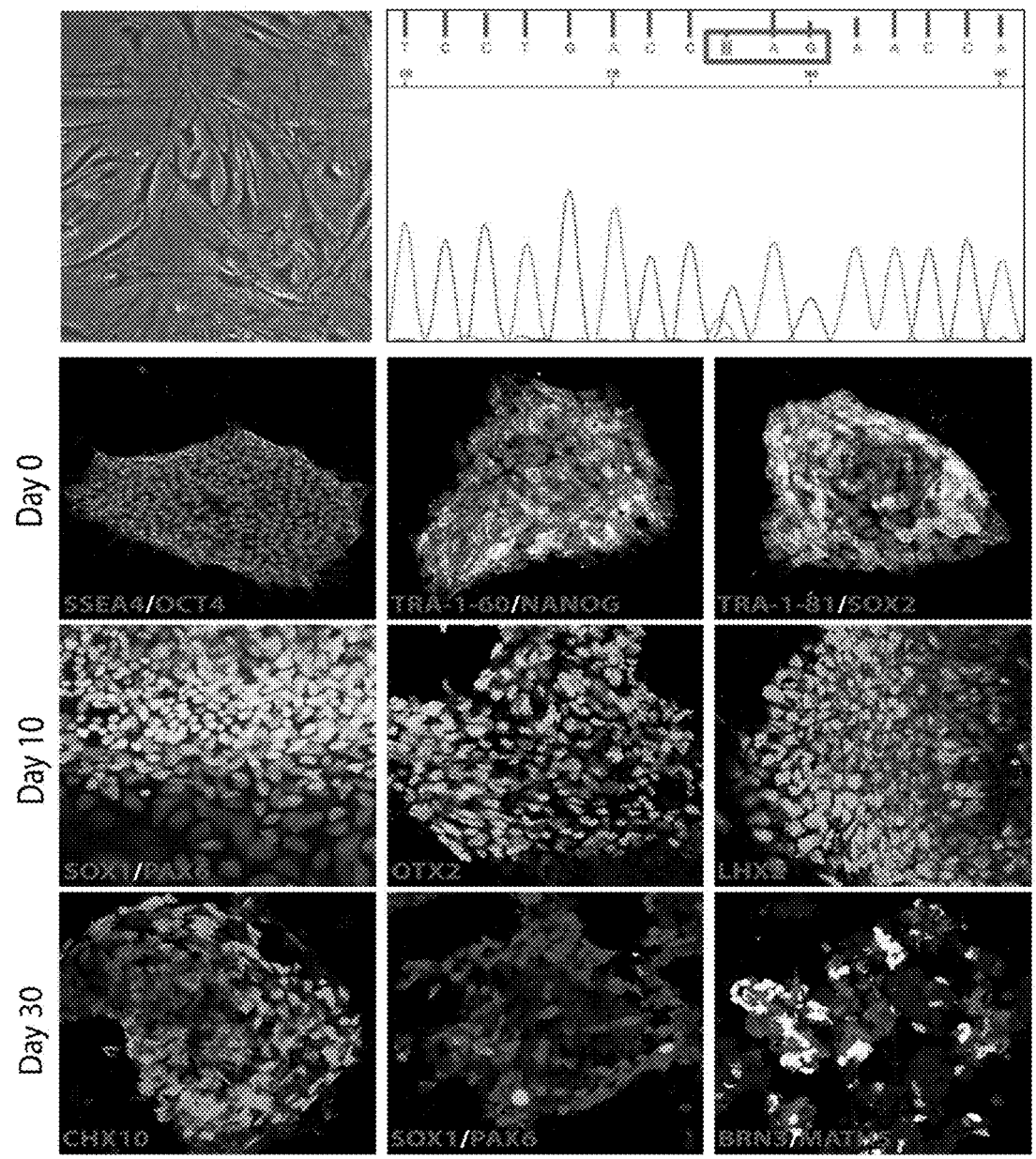
FIG. 10: Glaucoma hiPSCs. Fibroblasts from a glaucoma patient with an E50K mutation in the OPTN gene were reprogrammed to yield hiPSCs. These hiPSCs demonstrated immunoreactivity to pluripotency markers such as OCT4, SOX2, Nanog and the cell surface antigens SSEA4, Tra-1-81 and Tra-1-60. Cells were directed to differentiate and by day 10, expressed markers indicative of a neural progenitor state. By 30 days of differentiation, retinal progenitors were observed, as well as the onset of RGC-specification.
Figure 11:
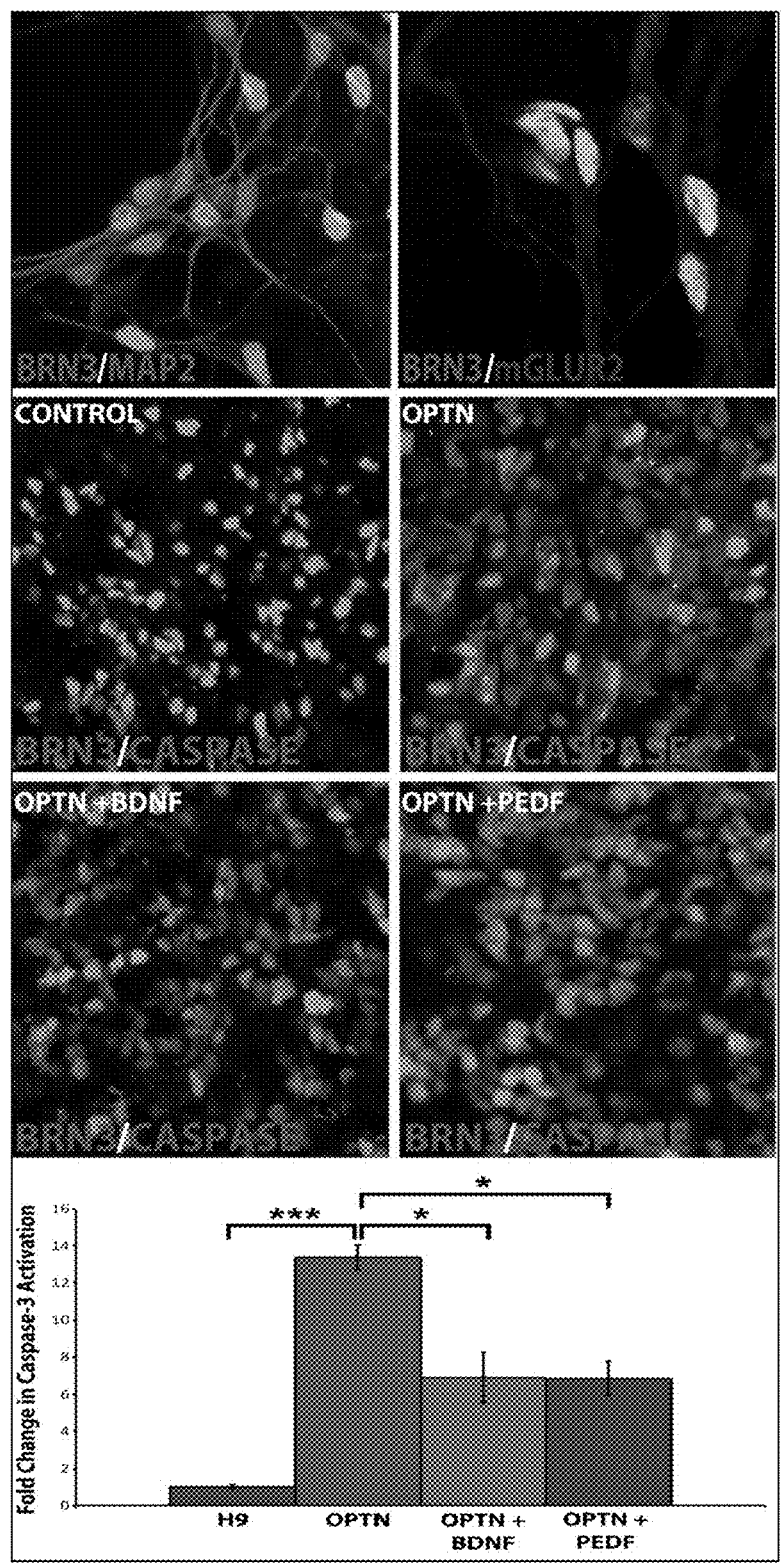
FIG. 11: Glaucoma IPS cell phenotype. Retinal ganglion cells were differentiated from OPTN patient hiPSCs as described. Immunocytochemistry analysis revealed widespread expression of BRN3 as well as the development of complex neural networks, indicated by MAP2 and mGLUR2. Untreated OPTN RGCs demonstrated elevated levels of apoptosis, as indicated by increased abundance of activated Caspase-3 when compared to an hiPSC control cell line. After treatment with growth factors BDNF or PEDF, levels of activated Caspase-3 were significantly reduced.

Multiple factors have been demonstrated to be associated with a glaucoma-related phenotype, with elevated levels of intraocular pressure perhaps the most widely recognized correlative factor leading to the degeneration of retinal ganglion cells. However, elevated intraocular pressure is not sufficient to explain many forms of glaucoma, particularly normal-tension primary open-angle glaucoma (nt-POAG). The ability to derive hiPSCs from nt-POAG patients represents a novel method to study inherent contributions to glaucomatous neurodegeneration in the absence of elevated intraocular pressure, creating a novel opportunity to identify and test factors contributing to a glaucoma phenotype. Mutations in the Optineurin (OPTN) gene lead to severe degeneration in RGCs and are uniquely suited for the in vitro study of glaucomatous neurodegeneration. Thus, the present disclosure provides a unique method of generating induced pluripotent stem cells (iPS) from glaucoma patients. As discussed above, and as illustrated in FIGS. 10 and 11 such cells provide a novel research and study tool.

The present invention relates generally to methods for producing populations of retinal ganglion cells (RGCs) from human pluripotent cells and RGCs and populations thereof generated using such methods.

In some embodiments, pluripotent cells are cultured under conditions that promote differentiation towards cells of the retinal lineage. Conditions for differentiating pluripotent cells towards cells of the retinal lineage have been described, such as, for example, in Meyer et al. (2011), which is incorporated herein by reference as if set forth in its entirety.

In one aspect, the inventors have unexpectedly found that modifying cell culture conditions and/or cell handling techniques, relative to known culturing and differentiation procedures, allows generation of pluripotent cell-derived RGCs and that such modifications increase survival of RGCs. For example, in some embodiments, the step of dissociating cells was found to be improved with the use of a mild enzyme treatment, such as ACCUTASE (a cell detachment solution of proteolytic & collagenolytic enzymes). By "mild enzyme", it is meant that the enzyme does not affect cell viability to a great extent. In some embodiments, plating cells at early differentiation stages in the presence of fetal bovine serum (FBS), rather than laminin, can increase the yield of RGCs produced, relative to previous methods. In some embodiments, undifferentiated cells are maintained in a defined medium, such as mTeSR1, which can improve the number of retinal cells that can be generated from the undifferentiated cells, relative to those maintained on feeder cells.

In some embodiments, using the culture conditions described above, retinal progenitor cells are generated, for example, by way of retinal neurosphere formation. The retinal progenitor cells are characterized by Chx10 and Pax6 expression and by an absence of Sox1 expression. Progenitor cells are observed from days 20 to 50 of differentiation. Just prior to differentiation into RGCs, progenitor retinal cells exhibit increased expression of Math5, a transcription factor required for RGC development. Upon differentiation into RGCs the cells are Brn3 positive.

Retinal ganglion cells made using methods of the present invention are characterized by one or more of the following:

i) molecular markers: increased expression of Brn3 and one or more of Map2, Math5 and Islet1; absence of γ-synuclein and/or Crx expression;

ii) morphological characteristics typical of RGCs, such as long neurite outgrowths; and iii) physiological characteristics: ability to fire action potentials, ability to exhibit inward sodium currents that are sensitive to a voltage-gated sodium channel blocker, and or ability to conduct potassium through voltage-gated channels.

In some embodiments, the disclosed methods for making RGC populations are applied to induced pluripotent stem (iPS) cells, thereby providing a method for generating patient-specific and/or disease-specific retinal ganglion cells. For example, fibroblasts derived from a patient with an E50K mutation in the Optineurin (Optn) gene were reprogrammed to yield lines of patient-specific iPS cells. These iPS cells were then differentiated toward a RGC-like fate, using methods provided herein, to produce Brn3-positive retinal ganglion-like cells. The iPS-derived RGC cells produced using the methods provided herein provide a model system for studying human retinogenesis and for developing patient-specific therapies for diseases affecting retinal ganglion cells, such as glaucoma and other optic neuropathies.

In some embodiments, isolated populations of RGCs produced using the methods provided herein are provided. In some embodiments, the RGC populations are purified.

Figure 12:
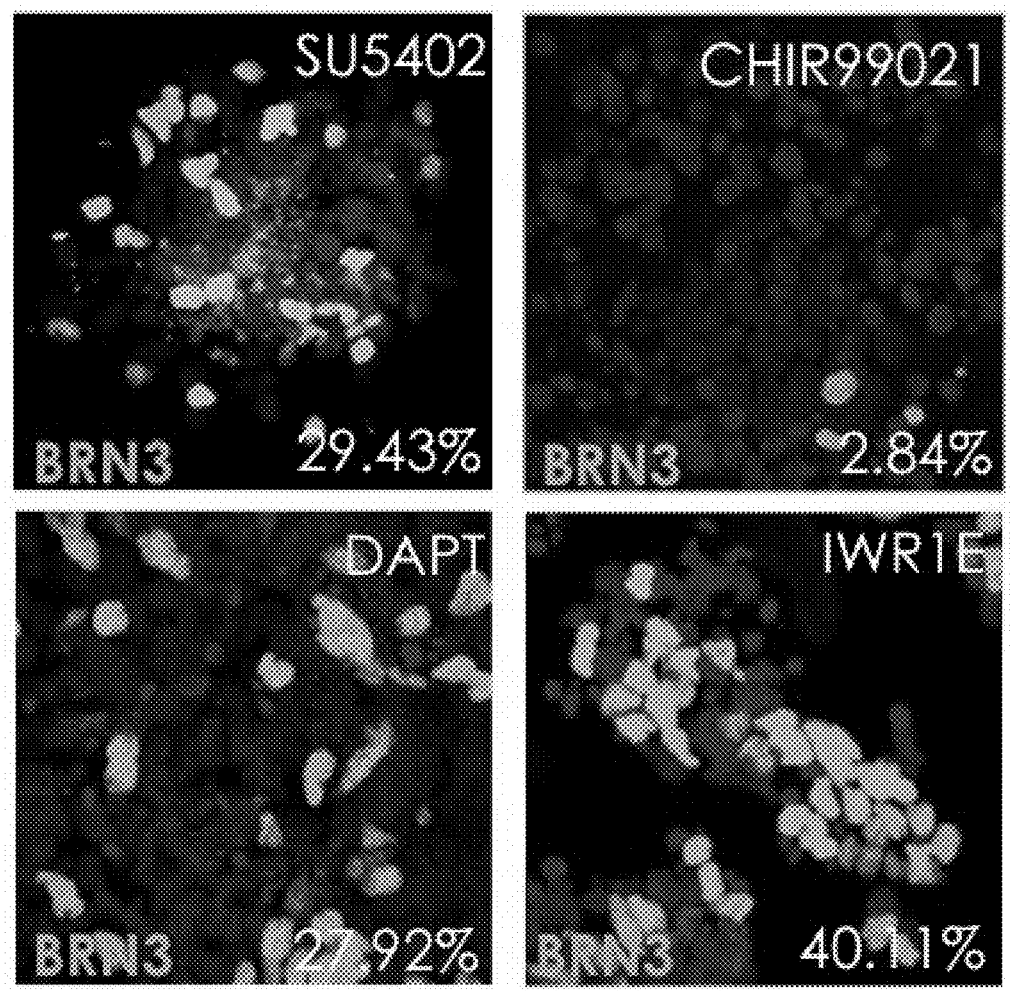
FIG. 12: Wnt RGC differentiation. Signaling mechanisms underlying RGC specification were tested, including the Notch, FGF, and Wnt signaling pathways. By inhibiting Notch signaling (DAPT treatment), no effects on RGC development were observed. By inhibiting FGF signaling (SU5402 treatment), no effects on RGC development were observed. By inhibiting Wnt signaling (IWR1E treatment), RGC development was enhanced, whereas activation of Wnt signaling (CHIR99021 treatment), greatly reduced RGC development.

A further feature of the disclosure is illustrated in FIG. 12, wherein the involvement of Wnt signalling on RGC differentiation was investigated. Specifically, as shown in FIG. 12, inhibition of Wnt signaling (IWR1E, or IWR-1-endo, treatment) was found to result in enhanced RGC development. Similarly, activation of Wnt signaling (CHIR99021 treatment) was found to greatly reduce RGC development. Thus, this finding provides a further enhancement to the presently described method of making RGCs.

Although the invention has been described with reference to certain specific embodiments, various modifications thereof will be apparent to those skilled in the art. Any examples provided herein are included solely for the purpose of illustrating the invention and are not intended to limit the invention in any way. Any drawings provided herein are solely for the purpose of illustrating various aspects of the invention and are not intended to be drawn to scale or to limit the invention in any way. The scope of the claims appended hereto should not be limited by the preferred embodiments set forth in the above description, but should be given the broadest interpretation consistent with the present specification as a whole. The disclosures of all references recited herein are incorporated herein by reference in their entirety.

REFERENCES

Al-Shamekh, S. and Goldberg, J. L. 2014. Retinal repair with induced pluripotent stem cells. Transl. Res. 163:377-386.

Badea, T. C. and Nathans, J. 2011. Morphologies of mouse retinal ganglion cells expressing transcription factors Brn3a, Brn3b, and Brn3c: Analysis of wild type and mutant cells using genetically-directed sparse labeling. Vision Res. 51:269-279.

Badea, T. C., Williams, J., Smallwood, P., Shi, M., Motajo, O., and Nathans, J. 2012. Combinatorial expression of Brn3 transcription factors in somatosensory neurons: Genetic and morphologic analysis. J. Neurosci. 32:995-1007.

Belecky-Adams, T., Tomarev, S., Li, H. S., Ploder, L., McInnes, R. R., Sundin, O., and Adler, R. 1997. Pax-6, Prox 1, and Chx10 homeobox gene expression correlates with phenotypic fate of retinal precursor cells. Invest. Ophthalmol. Vis. Sci. 38:1293-1303.

Bharti, K., Liu, W., Csermely, T., Bertuzzi, S., and Arnheiter, H. 2008. Alternative promoter use in eye development: The complex role and regulation of the transcription factor MITF. Development. 135:1169-1178.

Bryant, J., Goodyear, R. J., and Richardson, G. P. 2002. Sensory organ development in the inner ear: Molecular and cellular mechanisms. Br. Med. Bull. 63:39-57.

Buchholz, D. E., Hikita, S. T., Rowland, T. J., Friedrich, A. M., Hinman, C. R., Johnson, L. V., and Clegg, D. O. 2009. Derivation of functional retinal pigmented epithelium from induced pluripotent stem cells. Stem Cells 27:2427-2434.

Buchholz, D. E., Pennington, B. O., Croze, R. H., Hinman, C. R., Coffey, P. J., and Clegg, D. O. 2013. Rapid and efficient directed differentiation of human pluripotent stem cells into retinal pigmented epithelium. Stem Cells Transl. Med. 2:384-393.

Capowski, E. E., Simonett, J. M., Clark, E. M., Wright, L. S., Howden, S. E., Wallace, K. A., Petelinsek, A. M., Pinilla, I., Phillips, M. J., Meyer, J. S., Schneider, B. L., Thomson, J. A., and Gamm, D. M. 2014. Loss of MITF expression during human embryonic stem cell differentiation disrupts retinal pigment epithelium development and optic vesicle cell proliferation. Hum. Mol. Genet. 23:6332-6344.

Carr, A. J., Vugler, A. A., Hikita, S. T., Lawrence, J. M., Gias, C., Chen, L. L., Buchholz, D. E., Ahmado, A., Semo, M., Smart, M. J., Hasan, S., da Cruz, L., Johnson, L. V., Clegg, D. O., and Coffey, P. J. 2009. Protective effects of human iPS-derived retinal pigment epithelium cell transplantation in the retinal dystrophic rat. PLoS One 4:e8152.

Chambers, S. M., Qi, Y., Mica, Y., Lee, G., Zhang, X. J., Niu, L., Bilsland, J., Cao, L., Stevens, E., Whiting, P., Shi, S. H., and Studer, L. 2012. Combined small-molecule inhibition accelerates developmental timing and converts human pluripotent stem cells into nociceptors. Nat. Biotechnol. 30:715-720.

Ferrer, M., Corneo, B., Davis, J., Wan, Q., Miyagishima, K. J., King, R., Maminishkis, A., Marugan, J., Sharma, R., Shure, M., Temple, S., Miller, S., and Bharti, K. 2014. A multiplex high-throughput gene expression assay to simultaneously detect disease and functional markers in induced pluripotent stem cell-derived retinal pigment epithelium. Stem Cells Transl. Med. 3:911-922.

Fuhrmann, S., Levine, E. M., and Reh, T. A. 2000. Extraocular mesenchyme patterns the optic vesicle during early eye development in the embryonic chick. Development 127:4599-4609.

Gamm, D. M. and Meyer, J. S. 2010. Directed differentiation of human induced pluripotent stem cells: A retina perspective. Regen. Med. 5:315-317.

Gonzalez-Cordero, A., West, E. L., Pearson, R. A., Duran, Y., Carvalho, L. S., Chu, C. J., Naeem, A., Blackford, S. J., Georgiadis, A., Lakowski, J., Hubank, M., Smith, A. J., Bainbridge, J. W., Sowden, J. C., and Ali, R. R. 2013. Photoreceptor precursors derived from three-dimensional embryonic stem cell cultures integrate and mature within adult degenerate retina. Nat. Biotechnol. 31:741-747.

Hirami, Y., Osakada, F., Takahashi, K., Okita, K., Yamanaka, S., Ikeda, H., Yoshimura, N., and Takahashi, M. 2009. Generation of retinal cells from mouse and human induced pluripotent stem cells. Neurosci. Lett. 458:126-131.

Horsford, D. J., Nguyen, M. T., Sellar, G. C., Kothary, R., Arnheiter, H., and McInnes, R. R. 2005. Chx10 repression of Mitf is required for the maintenance of mammalian neuroretinal identity. Development 132:177-187.

Jin, Z. B., Okamoto, S., Osakada, F., Homma, K., Assawachananont, J., Hirami, Y., Iwata, T., and Takahashi, M. 2011. Modeling retinal degeneration using patient-specific induced pluripotent stem cells. PLoS One 6:e17084.

Jin, Z. B., Okamoto, S., Xiang, P., and Takahashi, M. 2012. Integration-free induced pluripotent stem cells derived from retinitis pigmentosa patient for disease modeling. Stem Cells Transl. Med. 1:503-509.

Lamba, D. A., Karl, M. O., Ware, C. B., and Reh, T. A. 2006. Efficient generation of retinal progenitor cells from human embryonic stem cells. Proc. Natl. Acad. Sci. U.S.A. 103:12769-12774.

Lamba, D. A., McUsic, A., Hirata, R. K., Wang, P. R., Russell, D., and Reh, T. A. 2010. Generation, purification and transplantation of photoreceptors derived from human induced pluripotent stem cells. PLoS One 5:e8763.

Liao, J. L., Yu, J., Huang, K., Hu, J., Diemer, T., Ma, Z., Dvash, T., Yang, X. J., Travis, G. H., Williams, D. S., Bok, D., and Fan, G. 2010. Molecular signature of primary retinal pigment epithelium and stem-cell-derived RPE cells. Hum. Mol. Genet. 19:4229-4238.

Livesey, F. J. and Cepko, C. L. 2001. Vertebrate neural cell-fate determination: Lessons from the retina. Nat. Rev. Neurosci. 2:109-118.

Ludwig, T. E., Bergendahl, V., Levenstein, M. E., Yu, J., Probasco, M. D., and Thomson, J. A. 2006. Feeder-independent culture of human embryonic stem cells. Nat. Methods 3:637-646.

Marquardt, T. and Gruss, P. 2002. Generating neuronal diversity in the retina: One for nearly all. Trends Neurosci. 25:32-38.

Martinez-Morales, J. R., Dolez, V., Rodrigo, I., Zaccarini, R., Leconte, L., Bovolenta, P., and Saule, S. 2003. OTX2 activates the molecular network underlying retina pigment epithelium differentiation. J. Biol. Chem. 278:21721-21731.

Maruotti, J., Wahlin, K., Gorrell, D., Bhutto, I., Lutty, G., and Zack, D. J. 2013. A simple and scalable process for the differentiation of retinal pigment epithelium from human pluripotent stem cells. Stem Cells Transl. Med. 2:341-354.

Mellough, C. B., Sernagor, E., Moreno-Gimeno, I., Steel, D. H., and Lako, M. 2012. Efficient stage-specific differentiation of human pluripotent stem cells toward retinal photoreceptor cells. Stem Cells 30:673-686.

Meyer, J. S., Shearer, R. L., Capowski, E. E., Wright, L. S., Wallace, K. A., McMillan, E. L., Zhang, S. C., and Gamm, D. M. 2009. Modeling early retinal development with human embryonic and induced pluripotent stem cells. Proc. Natl. Acad. Sci. U.S.A. 106:16698-16703.

Meyer, J. S., Howden, S. E., Wallace, K. A., Verhoeven, A. D., Wright, L. S., Capowski, E. E., Pinilla, I., Martin, J. M., Tian, S., Stewart, R., Pattnaik, B., Thomson, J. A., and Gamm, D. M. 2011. Optic vesicle-like structures derived from human pluripotent stem cells facilitate a customized approach to retinal disease treatment. Stem Cells 29:1206-1218.

Nakano, T., Ando, S., Takata, N., Kawada, M., Muguruma, K., Sekiguchi, K., Saito, K., Yonemura, S., Eiraku, M., and Sasai, Y. 2012. Self-formation of optic cups and storable stratified neural retina from human ESCs. Cell Stem Cell 10:771-785.

Oliver, G. and Gruss, P. 1997. Current views on eye development. Trends Neurosci. 20:415-421.

Osakada, F., Ikeda, H., Mandai, M., Wataya, T., Watanabe, K., Yoshimura, N., Akaike, A., Sasai, Y., and Takahashi, M. 2008. Toward the generation of rod and cone photoreceptors from mouse, monkey and human embryonic stem cells. Nat. Biotechnol. 26:215-224.

Park, I. H., Zhao, R., West, J. A., Yabuuchi, A., Huo, H., Ince, T. A., Lerou, P. H., Lensch, M. W., and Daley, G. Q. 2008. Reprogramming of human somatic cells to pluripotency with defined factors. Nature 451:141-146.

Phillips, M. J., Wallace, K. A., Dickerson, S. J., Miller, M. J., Verhoeven, A. D., Martin, J. M., Wright, L. S., Shen, W., Capowski, E. E., Percin, E. F., Perez, E. T., Zhong, X., Canto-Soler, M. V., and Gamm, D. M. 2012. Blood-derived human iPS cells generate optic vesicle-like structures with the capacity to form retinal laminae and develop synapses. Invest. Ophthalmol. Vis. Sci. 53:2007-2019.

Phillips, M. J., Perez, E. T., Martin, J. M., Reshel, S. T., Wallace, K. A., Capowski, E. E., Singh, R., Wright, L. S., Clark, E. M., Barney, P. M., Stewart, R., Dickerson, S. J., Miller, M. J., Percin, E. F., Thomson, J. A., and Gamm, D. M. 2014. Modeling human retinal development with patient-specific induced pluripotent stem cells reveals multiple roles for visual system homeobox 2. Stem Cells 32:1480-1492.

Reichman, S., Terray, A., Slembrouck, A., Nanteau, C., Orieux, G., Habeler, W., Nandrot, E. F., Sahel, J. A., Monville, C., and Goureau, O. 2014. From confluent human iPS cells to self-forming neural retina and retinal pigmented epithelium. Proc. Natl. Acad. Sci. U.S.A. 111:8518-8523.

Rowan, S., Chen, C. M., Young, T. L., Fisher, D. E., and Cepko, C. L. 2004. Transdifferentiation of the retina into pigmented cells in ocular retardation mice defines a new function of the homeodomain gene Chx10. Development 131:5139-5152.

Rowland, T. J., Blaschke, A. J., Buchholz, D. E., Hikita, S. T., Johnson, L. V., and Clegg, D. O. 2013. Differentiation of human pluripotent stem cells to retinal pigmented epithelium in defined conditions using purified extracellular matrix proteins. J. Tissue Eng. Regen. Med. 7:642-653.

Shi, M., Kumar, S. R., Motajo, O., Kretschmer, F., Mu, X., and Badea, T. C. 2013. Genetic interactions between Brn3 transcription factors in retinal ganglion cell type specification. PLoS One 8:e76347.

Shibahara, S., Yasumoto, K., Amae, S., Udono, T., Watanabe, K., Saito, H., and Takeda, K. 2000. Regulation of pigment cell-specific gene expression by MITF. Pigment. Cell Res. 13:98-102.

Singh, R., Phillips, M. J., Kuai, D., Meyer, J., Martin, J. M., Smith, M. A., Perez, E. T., Shen, W., Wallace, K. A., Capowski, E. E., Wright, L. S., and Gamm, D. M. 2013a. Functional analysis of serially expanded human iPS cell-derived RPE cultures. Invest Ophthalmol. Vis. Sci. 54:6767-6778.

Singh, R., Shen, W., Kuai, D., Martin, J. M., Guo, X., Smith, M. A., Perez, E. T., Phillips, M. J., Simonett, J. M., Wallace, K. A., Verhoeven, A. D., Capowski, E. E., Zhang, X., Yin, Y., Halbach, P. J., Fishman, G. A., Wright, L. S., Pattnaik, B. R., and Gamm, D. M. 2013b. iPS cell modeling of Best disease: Insights into the pathophysiology of an inherited macular degeneration. Hum. Mol. Genet. 22:593-607.

Sridhar, A., Steward, M. M., and Meyer, J. S. 2013. Nonxenogeneic growth and retinal differentiation of human induced pluripotent stem cells. Stem Cells Transl. Med. 2:255-264.

Stern, J. and Temple, S. 2014. Stem cells for retinal repair. Dev. Ophthalmol. 53:70-80.

Takahashi, K., Tanabe, K., Ohnuki, M., Narita, M., Ichisaka, T., Tomoda, K., and Yamanaka, S. 2007. Induction of pluripotent stem cells from adult human fibroblasts by defined factors. Cell 131:861-872.

Thomson, J. A., Itskovitz-Eldor, J., Shapiro, S. S., Waknitz, M. A., Swiergiel, J. J., Marshall, V. S., and Jones, J. M. 1998. Embryonic stem cell lines derived from human blastocysts. Science 282:1145-1147.

Tucker, B. A., Anfinson, K. R., Mullins, R. F., Stone, E. M., and Young, M. J. 2013a. Use of a synthetic xeno-free culture substrate for induced pluripotent stem cell induction and retinal differentiation. Stem Cells Transl. Med. 2:16-24.

Tucker, B. A., Mullins, R. F., Streb, L. M., Anfinson, K., Eyestone, M. E., Kaalberg, E., Riker, M. J., Drack, A. V., Braun, T. A., and Stone, E. M. 2013b. Patient-specific iPSC-derived photoreceptor precursor cells as a means to investigate retinitis pigmentosa. Elife. (Cambridge)2: e00824.

Vugler, A., Carr, A. J., Lawrence, J., Chen, L. L., Burrell, K., Wright, A., Lundh, P., Semo, M., Ahmado, A., Gias, C., da Cruz, L., Moore, H., Andrews, P., Walsh, J., and Coffey, P. 2008. Elucidating the phenomenon of HESC-derived RPE: Anatomy of cell genesis, expansion and retinal transplantation. Exp. Neurol. 214:347-361.

Wahlin, K. J., Maruotti, J., and Zack, D. J. 2014. Modeling retinal dystrophies using patient-derived induced pluripotent stem cells. Adv. Exp. Med. Biol. 801:157-164.

Weir, J., Rivolta, M., and Holley, M. 2000. Identification of differentiating cochlear hair cells in vitro. Am. J. Otol. 21:130-134.

Wright, L. S., Phillips, M. J., Pinilla, I., Hei, D., and Gamm, D. M. 2014. Induced pluripotent stem cells as custom therapeutics for retinal repair: Progress and rationale. Exp. Eye. Res. 123:161-172.

Yu, J., Vodyanik, M. A., Smuga-Otto, K., Antosiewicz-Bourget, J., Frane, J. L., Tian, S., Nie, J., Jonsdottir, G. A., Ruotti, V., Stewart, R., Slukvin, II, and Thomson, J. A. 2007. Induced pluripotent stem cell lines derived from human somatic cells. Science 318:1917-1920.

Zhang, S. S., Fu, X. Y., and Barnstable, C. J. 2002. Molecular aspects of vertebrate retinal development. Mol. Neurobiol. 26:137-152.

Zhong, X., Gutierrez, C., Xue, T., Hampton, C., Vergara, M. N., Cao, L. H., Peters, A., Park, T. S., Zambidis, E. T., Meyer, J. S., Gamm, D. M., Yau, K. W., and Canto-Soler, M. V. 2014. Generation of three-dimensional retinal tissue with functional photoreceptors from human iPSCs. Nat. Commun. 5:4047.

Tables

TABLE 1

Primary Antibodies for Immunocytochemistry

| Antibody | Source | Catalog number | Dilution |
|---|---|---|---|
| βIII tubulin | Covance | PRB-435P | 1:100 |
| Brn3 | Santa Cruz Biotechnology | SC-6026 | 1:200 |
| Chx10 | Santa Cruz Biotechnology | SC-21690 | 1:200 |
| Crx | Abnova | H00001406-M02 | 1:100 |
| Dlx5 | Abcam | Ab64827 | 1:200 |
| Ki-67 | BD Biosciences | 556003 | 1:500 |
| Lhx2 | Santa Cruz Biotechnology | SC-19344 | 1:200 |
| Map2 | Santa Cruz Biotechnology | SC-20172 | 1:200 |
| Nanog | R&D Systems | AF1997 | 1:100 |
| Oct4 | Stemgent | 09-0023 | 1:200 |
| Otx2 | R & D Systems | AF1979 | 1:2000 |
| Pax6 | Developmental Studies Hybridoma Bank | PAX6 | 1:50 |
| Recoverin | Chemicon | AB5585 | 1:2000 |
| Sox1 | R & D Systems | AF3369 | 1:1000 |
| Sox2 | R & D Systems | AF2018 | 1:1000 |
| SSEA-4 | Chemicon | 09-0006 | 1:500 |
| Tra-1-60 | Chemicon | 09-0010 | 1:1000 |
| Tra-1-81 | Chemicon | 09-0011 | 1:1000 |
| ZO-1 | Zymed | 61-7300 | 1:100 |

TABLE 2

Primers for RT-PCR and Quantitative RT-PCR

| Gene amplified | Forward | Reverse | Size (bp) |
|---|---|---|---|
| α-Fetoprotein | AGA ACC TGT CAC AAG CTG TG | GAC AGC AAG CTG AGG ATG TC | 676 |
| ARRESTIN | ACA AGC TAG GGG ACA ATG CC | TTG TGC TAG AGG CCA GGT TG | 597 |
| BEST1 | GGT GTG GTT TGC CAA CCT GTC AAT | TGT TCA TCT CGT TCA GCA GGC TCT | 92 |
| BRACHYURY | ACC CAG TTC ATA GCG GTG AC | CAA TTG TCA TGG GAT TGC AG | 218 |
| BRN3 | CTC ACA CTG TCC CAC AAT AAT A | CCG GCG AAA TAT TTC ATT CT | 311 |
| CHX10 | ATT CAA CGA AGC CCA CTA CCC AGA | ATC CTT GGC TGA CTT GAG GAT GGA | 229 |
| CRX | TAT TCT GTC AAC GCC TTG GCC CTA | TGC ATT TAG CCC TCC GGT TCT TGA | 253 |
| DLX1 | CAA CCA GCA AAT GTC TCC TTC TC | CGC ACT TCA CCG CCT TCC | 282 |
| EMX1 | AGA CGC AGG TGA AGG TGT GG | CAG GCA GGC AGG CTC TCC | 403 |
| EZRIN | ACC ACC ATG GAT GCA GAG CTG GA | ACA CTT CCC GGA GGC CGA TAG T | 100 |
| FABP7 | AGG CAG GTG GGA AAT GTG AC | CAT AGT GGC GAA CAG CAA CC | 298 |
| ISLET1 | GTG TGA TCC GGG TCT GGT TT | AAT TAG AGC CCG TCC CTC CT | 300 |
| KLF4 | AGT CCC GCC GCT CCA TTA CCA A | TGC TCG GTC GCA TTT TTG GCA C | 316 |
| LHX2 | CAA GAT CTC GGA CCG CTA CT | CCG TGG TCA GCA TCT TGT TA | 284 |
| LIN28 | AGT GGT TCA ACG TGC GCA TGG G | AGG TCC GGT GAC ACG GAT GGA T | 203 |
| NANOG | CAA AGG CAA ACA ACC CAC TT | TCT GCT GGA GGC TGA GGT AT | 158 |
| NEUROD1 | TAC TGC TGC AAA GTG CAA ATA C | AAG TGC TAA GGC AAC ACA ATA AC | 539 |

TABLE 2-continued

Primers for RT-PCR and Quantitative RT-PCR

| Gene amplified | Forward | Reverse | Size (bp) |
|---|---|---|---|
| NEUROD4 | AGG TCT GGG CTC CCA AAA TG | GCC CCG GAG ACT GAT AGT TG | 557 |
| OCT4 | CGA GCA ATT TGC CAA GCT CCT GAA | TTC GGG CAC TGC AGG AAC AAA TTC | 324 |
| OPSIN | GAA GTT CAA GAA GCT GCG CC | TCT CAC ATT GCC AAA GGG CT | 253 |
| OTX2 | CAA CAG CAG AAT GGA GGT CA TG | CTG GGT GGA AAG AGA GAA GC | 429 |
| PAX6 | CGG AGT GAA TCA GCT CGG TG | CCG CTT ATA CTG GGC TAT TTT GC | 300 (+5a) 258 (−5a) |
| PEDF | AGA TCT CAG CTG CAA GAT TGC CCA | ATG AAT GAA CTC GGA GGT GAG GCT | 127 |
| RAX | GAA TCT CGA AAT CTC AGC CC | CTT CAC TAA TTT GCT CAG GAC | 279 |
| RPE65 | TAC CAC AGA AGG TTC ATC CGC ACT | GGG AAA GCA CAG GTG CCA AAT TCT | 92 |
| SIX3 | CGA GCA GAA GAC GCA TTG CTT CAA | CGG CCT TGG CTA TCA TAC ATC ACA | 394 |
| SIX6 | ATT TGG GAC GGC GAA CAG AAG ACA | ATC CTG GAT GGG CAA CTC AGA TGT | 385 |
| SOX1 | CAA TGC GGG GAG GAG AAG TC | CTC TGG ACC AAA CTG TGG CG | 464 |
| SOX2 | CCC CCG GCG GCA ATA GCA | TCG GCG CCG GGG AGA TAC AT | 448 |
| TRANSDUCIN | CAC GAT GCC AAA GGA GAT GT | GGT GGT TGC AGA TGC TGT TG | 419 |

35

TABLE 3

Troubleshooting Guide

| Problem | Possible Cause | Solution |
|---|---|---|
| EB survival is low after passaging | Pipetting too vigorously to remove cells from plates | Leave dispase on hPSCs longer to ensure easy detachment of cells |
| | Cells are aspirated with supernatant | Allow cells to settle at least 5 min by gravity or centrifuge for 1 min at 100 × g |
| Neurosphere yield is low | Cells were not plated densely enough with FBS | Increase density upon next plating |
| Cells do not adhere to plates with 10% FBS | Too much NIM was added, resulting in <10% final FBS | Instead of changing the medium, add 5% more FBS to each well and return to incubator overnight. Change medium the following day and add fresh NIM to each well. |
| Undifferentiated cells grow too slowly | Cells were broken up too much during passaging | At next passage, pipet cells fewer times to break up cell aggregates, then increase this number with each subsequent passage |
| Colonies take too long (15-20 min) to detach from plate | Dispase is not warm | Allow dispase to warm in 37° C. water bath for 15 min |
| | Dispase powder did not completely dissolve when solution was made | When making dispase, add powder to warm DMEM/F12 and allow enzyme to dissolve at 37° C. for at least 20 min |
| Recently plated undifferentiated hPSCs or EBs are not evenly distributed across well | Plates were not agitated when placed in the incubator or were disturbed by opening/closing the incubator | Agitate plates front-to-back and side-to-side in short, quick movements to ensure an even distribution of cells on the well surface. Place plates near the back of the incubator to minimize disturbance. |

We claim:

1. A method of making human retinal ganglion cells, comprising:
   (a) differentiating human pluripotent stem cells into retinal progenitor by contacting the human pluripotent stem cells with a neural induction medium, wherein the retinol progenitor cells lack Sox1 expression; and
   (b) differentiating the retinal progenitor cells into retinal ganglion cells by contacting the retinal progenitor cells with a retinal differentiation medium.

2. The method of claim 1, wherein the retinal progenitor cells express Chx10 and/or Pax6.

3. The method of claim 1, wherein the retinal ganglion cells have one or more of the following features:
   retinal ganglion cell morphology;
   ability to fire action potentials;
   ability to exhibit inward sodium currents that are sensitive to a voltage-gated sodium channel blocker;
   ability to conduct potassium through voltage-gated channels; and
   Brn3 expression.

4. The method of claim 1, wherein the retinal progenitor cells are treated with a enzyme to dissociate said progenitor cells.

5. The method of claim 1, wherein the pluripotent stem cells or retinal progenitor cells are plated in the presence of fetal bovine serum.

6. The method of claim 1, wherein undifferentiated retinal progenitor cells or undifferentiated retinal ganglion cells are maintained in mTeSR1 medium.

7. The method of claim 1, wherein the pluripotent stem cells are human pluripotent stem cells or human induced pluripotent stem cells.

8. The method of claim 1, wherein the pluripotent stem cells are from a glaucoma patient-specific line of human induced pluripotent stem cells.

9. The method of claim 1, wherein, prior to differentiation of the retinal progenitor cells, the method includes the step of inhibiting Wnt signaling.

10. The method of claim 9, wherein Wnt signaling is inhibited by treatment with an inhibitor.

11. The method of claim 10, wherein the inhibitor is IWR1E.

* * * * *

SEQUENCE LISTING

<160> NUMBER OF SEQ ID NOS: 60

<210> SEQ ID NO 1
<211> LENGTH: 20
<212> TYPE: DNA
<213> ORGANISM: Artificial Sequence
<220> FEATURE:
<223> OTHER INFORMATION: Synthetic primer

<400> SEQUENCE: 1
agaacctgtc acaagctgtg                                                   20

<210> SEQ ID NO 2
<211> LENGTH: 20
<212> TYPE: DNA
<213> ORGANISM: Artificial Sequence
<220> FEATURE:
<223> OTHER INFORMATION: Synthetic primer

<400> SEQUENCE: 2
gacagcaagc tgaggatgtc                                                   20

<210> SEQ ID NO 3
<211> LENGTH: 20
<212> TYPE: DNA
<213> ORGANISM: Artificial Sequence
<220> FEATURE:
<223> OTHER INFORMATION: Synthetic primer

<400> SEQUENCE: 3
acaagctagg ggacaatgcc                                                   20

<210> SEQ ID NO 4
<211> LENGTH: 20
<212> TYPE: DNA
<213> ORGANISM: Artificial Sequence
<220> FEATURE:
<223> OTHER INFORMATION: Synthetic primer

<400> SEQUENCE: 4
ttgtgctaga ggccaggttg                                                   20

<210> SEQ ID NO 5
<211> LENGTH: 24
<212> TYPE: DNA
<213> ORGANISM: Artificial Sequence
<220> FEATURE:
<223> OTHER INFORMATION: Synthetic primer

<400> SEQUENCE: 5
ggtgtggttt gccaacctgt caat                                              24

<210> SEQ ID NO 6
<211> LENGTH: 24
<212> TYPE: DNA
<213> ORGANISM: Artificial Sequence
<220> FEATURE:
<223> OTHER INFORMATION: Synthetic primer

<400> SEQUENCE: 6
tgttcatctc gttcagcagg ctct                                              24

<210> SEQ ID NO 7
<211> LENGTH: 20
<212> TYPE: DNA
<213> ORGANISM: Artificial Sequence

```
<220> FEATURE:
<223> OTHER INFORMATION: Synthetic primer

<400> SEQUENCE: 7
acccagttca tagcggtgac                                                    20

<210> SEQ ID NO 8
<211> LENGTH: 20
<212> TYPE: DNA
<213> ORGANISM: Artificial Sequence
<220> FEATURE:
<223> OTHER INFORMATION: Synthetic primer

<400> SEQUENCE: 8
caattgtcat gggattgcag                                                    20

<210> SEQ ID NO 9
<211> LENGTH: 22
<212> TYPE: DNA
<213> ORGANISM: Artificial Sequence
<220> FEATURE:
<223> OTHER INFORMATION: Synthetic primer

<400> SEQUENCE: 9
ctcacactgt cccacaataa ta                                                 22

<210> SEQ ID NO 10
<211> LENGTH: 20
<212> TYPE: DNA
<213> ORGANISM: Artificial Sequence
<220> FEATURE:
<223> OTHER INFORMATION: Synthetic primer

<400> SEQUENCE: 10
ccggcggaat atttcattct                                                    20

<210> SEQ ID NO 11
<211> LENGTH: 24
<212> TYPE: DNA
<213> ORGANISM: Artificial Sequence
<220> FEATURE:
<223> OTHER INFORMATION: Synthetic primer

<400> SEQUENCE: 11
attcaacgaa gcccactacc caga                                               24

<210> SEQ ID NO 12
<211> LENGTH: 24
<212> TYPE: DNA
<213> ORGANISM: Artificial Sequence
<220> FEATURE:
<223> OTHER INFORMATION: Synthetic primer

<400> SEQUENCE: 12
atccttggct gacttgagga tgga                                               24

<210> SEQ ID NO 13
<211> LENGTH: 24
<212> TYPE: DNA
<213> ORGANISM: Artificial Sequence
<220> FEATURE:
<223> OTHER INFORMATION: Synthetic primer

<400> SEQUENCE: 13
tattctgtca acgccttggc ccta                                               24
```

```
<210> SEQ ID NO 14
<211> LENGTH: 24
<212> TYPE: DNA
<213> ORGANISM: Artificial Sequence
<220> FEATURE:
<223> OTHER INFORMATION: Synthetic primer

<400> SEQUENCE: 14
tgcatttagc cctccggttc ttga                                              24

<210> SEQ ID NO 15
<211> LENGTH: 23
<212> TYPE: DNA
<213> ORGANISM: Artificial Sequence
<220> FEATURE:
<223> OTHER INFORMATION: Synthetic primer

<400> SEQUENCE: 15
caaccagcaa atgtctcctt ctc                                               23

<210> SEQ ID NO 16
<211> LENGTH: 18
<212> TYPE: DNA
<213> ORGANISM: Artificial Sequence
<220> FEATURE:
<223> OTHER INFORMATION: Synthetic primer

<400> SEQUENCE: 16
cgcacttcac cgccttcc                                                     18

<210> SEQ ID NO 17
<211> LENGTH: 20
<212> TYPE: DNA
<213> ORGANISM: Artificial Sequence
<220> FEATURE:
<223> OTHER INFORMATION: Synthetic primer

<400> SEQUENCE: 17
agacgcaggt gaaggtgtgg                                                   20

<210> SEQ ID NO 18
<211> LENGTH: 18
<212> TYPE: DNA
<213> ORGANISM: Artificial Sequence
<220> FEATURE:
<223> OTHER INFORMATION: Synthetic primer

<400> SEQUENCE: 18
caggcaggca ggctctcc                                                     18

<210> SEQ ID NO 19
<211> LENGTH: 23
<212> TYPE: DNA
<213> ORGANISM: Artificial Sequence
<220> FEATURE:
<223> OTHER INFORMATION: Synthetic primer

<400> SEQUENCE: 19
accaccatgg atgcagagct gga                                               23

<210> SEQ ID NO 20
<211> LENGTH: 22
<212> TYPE: DNA
<213> ORGANISM: Artificial Sequence
<220> FEATURE:
<223> OTHER INFORMATION: Synthetic primer
```

-continued

```
<400> SEQUENCE: 20
acacttcccg gaggccgata gt                                              22

<210> SEQ ID NO 21
<211> LENGTH: 20
<212> TYPE: DNA
<213> ORGANISM: Artificial Sequence
<220> FEATURE:
<223> OTHER INFORMATION: Synthetic primer

<400> SEQUENCE: 21
aggcaggtgg gaaatgtgac                                                 20

<210> SEQ ID NO 22
<211> LENGTH: 20
<212> TYPE: DNA
<213> ORGANISM: Artificial Sequence
<220> FEATURE:
<223> OTHER INFORMATION: Synthetic primer

<400> SEQUENCE: 22
catagtggcg aacagcaacc                                                 20

<210> SEQ ID NO 23
<211> LENGTH: 20
<212> TYPE: DNA
<213> ORGANISM: Artificial Sequence
<220> FEATURE:
<223> OTHER INFORMATION: Synthetic primer

<400> SEQUENCE: 23
gtgtgatccg ggtctggttt                                                 20

<210> SEQ ID NO 24
<211> LENGTH: 20
<212> TYPE: DNA
<213> ORGANISM: Artificial Sequence
<220> FEATURE:
<223> OTHER INFORMATION: Synthetic primer

<400> SEQUENCE: 24
aattagagcc cggtcctcct                                                 20

<210> SEQ ID NO 25
<211> LENGTH: 22
<212> TYPE: DNA
<213> ORGANISM: Artificial Sequence
<220> FEATURE:
<223> OTHER INFORMATION: Synthetic primer

<400> SEQUENCE: 25
agtcccgccg ctccattacc aa                                              22

<210> SEQ ID NO 26
<211> LENGTH: 22
<212> TYPE: DNA
<213> ORGANISM: Artificial Sequence
<220> FEATURE:
<223> OTHER INFORMATION: Synthetic primer

<400> SEQUENCE: 26
tgctcggtcg cattttggc ac                                               22

<210> SEQ ID NO 27
```

```
<211> LENGTH: 20
<212> TYPE: DNA
<213> ORGANISM: Artificial Sequence
<220> FEATURE:
<223> OTHER INFORMATION: Synthetic primer

<400> SEQUENCE: 27
caagatctcg gaccgctact                                               20

<210> SEQ ID NO 28
<211> LENGTH: 20
<212> TYPE: DNA
<213> ORGANISM: Artificial Sequence
<220> FEATURE:
<223> OTHER INFORMATION: Synthetic primer

<400> SEQUENCE: 28
ccgtggtcag catcttgtta                                               20

<210> SEQ ID NO 29
<211> LENGTH: 22
<212> TYPE: DNA
<213> ORGANISM: Artificial Sequence
<220> FEATURE:
<223> OTHER INFORMATION: Synthetic primer

<400> SEQUENCE: 29
agtggttcaa cgtgcgcatg gg                                            22

<210> SEQ ID NO 30
<211> LENGTH: 22
<212> TYPE: DNA
<213> ORGANISM: Artificial Sequence
<220> FEATURE:
<223> OTHER INFORMATION: Synthetic primer

<400> SEQUENCE: 30
aggtccggtg acacggatgg at                                            22

<210> SEQ ID NO 31
<211> LENGTH: 20
<212> TYPE: DNA
<213> ORGANISM: Artificial Sequence
<220> FEATURE:
<223> OTHER INFORMATION: Synthetic primer

<400> SEQUENCE: 31
caaaggcaaa caacccactt                                               20

<210> SEQ ID NO 32
<211> LENGTH: 20
<212> TYPE: DNA
<213> ORGANISM: Artificial Sequence
<220> FEATURE:
<223> OTHER INFORMATION: Synthetic primer

<400> SEQUENCE: 32
tctgctggag gctgaggtat                                               20

<210> SEQ ID NO 33
<211> LENGTH: 22
<212> TYPE: DNA
<213> ORGANISM: Artificial Sequence
<220> FEATURE:
<223> OTHER INFORMATION: Synthetic primer

<400> SEQUENCE: 33
```
tactgctgca aagtgcaaat ac                                            22

<210> SEQ ID NO 34
<211> LENGTH: 23
<212> TYPE: DNA
<213> ORGANISM: Artificial Sequence
<220> FEATURE:
<223> OTHER INFORMATION: Synthetic primer

<400> SEQUENCE: 34
aagtgctaag gcaacacaat aac                                           23

<210> SEQ ID NO 35
<211> LENGTH: 20
<212> TYPE: DNA
<213> ORGANISM: Artificial Sequence
<220> FEATURE:
<223> OTHER INFORMATION: Synthetic primer

<400> SEQUENCE: 35
aggtctgggc tcccaaaatg                                               20

<210> SEQ ID NO 36
<211> LENGTH: 20
<212> TYPE: DNA
<213> ORGANISM: Artificial Sequence
<220> FEATURE:
<223> OTHER INFORMATION: Synthetic primer

<400> SEQUENCE: 36
gccccggaga ctgatagttg                                               20

<210> SEQ ID NO 37
<211> LENGTH: 24
<212> TYPE: DNA
<213> ORGANISM: Artificial Sequence
<220> FEATURE:
<223> OTHER INFORMATION: Synthetic primer

<400> SEQUENCE: 37
cgagcaattt gccaagctcc tgaa                                          24

<210> SEQ ID NO 38
<211> LENGTH: 24
<212> TYPE: DNA
<213> ORGANISM: Artificial Sequence
<220> FEATURE:
<223> OTHER INFORMATION: Synthetic primer

<400> SEQUENCE: 38
ttcgggcact gcaggaacaa attc                                          24

<210> SEQ ID NO 39
<211> LENGTH: 20
<212> TYPE: DNA
<213> ORGANISM: Artificial Sequence
<220> FEATURE:
<223> OTHER INFORMATION: Synthetic primer

<400> SEQUENCE: 39
gaagttcaag aagctgcgcc                                               20

<210> SEQ ID NO 40
<211> LENGTH: 20
<212> TYPE: DNA

```
<213> ORGANISM: Artificial Sequence
<220> FEATURE:
<223> OTHER INFORMATION: Synthetic primer

<400> SEQUENCE: 40
tctcacattg ccaaagggct                                                     20

<210> SEQ ID NO 41
<211> LENGTH: 20
<212> TYPE: DNA
<213> ORGANISM: Artificial Sequence
<220> FEATURE:
<223> OTHER INFORMATION: Synthetic primer

<400> SEQUENCE: 41
caacagcaga atggaggtca                                                     20

<210> SEQ ID NO 42
<211> LENGTH: 22
<212> TYPE: DNA
<213> ORGANISM: Artificial Sequence
<220> FEATURE:
<223> OTHER INFORMATION: Synthetic primer

<400> SEQUENCE: 42
ctgggtggaa agagagaagc tg                                                  22

<210> SEQ ID NO 43
<211> LENGTH: 20
<212> TYPE: DNA
<213> ORGANISM: Artificial Sequence
<220> FEATURE:
<223> OTHER INFORMATION: Synthetic primer

<400> SEQUENCE: 43
cggagtgaat cagctcggtg                                                     20

<210> SEQ ID NO 44
<211> LENGTH: 23
<212> TYPE: DNA
<213> ORGANISM: Artificial Sequence
<220> FEATURE:
<223> OTHER INFORMATION: Synthetic primer

<400> SEQUENCE: 44
ccgcttatac tgggctattt tgc                                                 23

<210> SEQ ID NO 45
<211> LENGTH: 24
<212> TYPE: DNA
<213> ORGANISM: Artificial Sequence
<220> FEATURE:
<223> OTHER INFORMATION: Synthetic primer

<400> SEQUENCE: 45
agatctcagc tgcaagattg ccca                                                24

<210> SEQ ID NO 46
<211> LENGTH: 24
<212> TYPE: DNA
<213> ORGANISM: Artificial Sequence
<220> FEATURE:
<223> OTHER INFORMATION: Synthetic primer

<400> SEQUENCE: 46
atgaatgaac tcggaggtga ggct                                                24
```

-continued

<210> SEQ ID NO 47
<211> LENGTH: 20
<212> TYPE: DNA
<213> ORGANISM: Artificial Sequence
<220> FEATURE:
<223> OTHER INFORMATION: Synthetic primer

<400> SEQUENCE: 47
gaatctcgaa atctcagccc                                              20

<210> SEQ ID NO 48
<211> LENGTH: 21
<212> TYPE: DNA
<213> ORGANISM: Artificial Sequence
<220> FEATURE:
<223> OTHER INFORMATION: Synthetic primer

<400> SEQUENCE: 48
cttcactaat ttgctcagga c                                            21

<210> SEQ ID NO 49
<211> LENGTH: 24
<212> TYPE: DNA
<213> ORGANISM: Artificial Sequence
<220> FEATURE:
<223> OTHER INFORMATION: Synthetic primer

<400> SEQUENCE: 49
taccacagaa ggttcatccg cact                                         24

<210> SEQ ID NO 50
<211> LENGTH: 24
<212> TYPE: DNA
<213> ORGANISM: Artificial Sequence
<220> FEATURE:
<223> OTHER INFORMATION: Synthetic primer

<400> SEQUENCE: 50
gggaaagcac aggtgccaaa ttct                                         24

<210> SEQ ID NO 51
<211> LENGTH: 24
<212> TYPE: DNA
<213> ORGANISM: Artificial Sequence
<220> FEATURE:
<223> OTHER INFORMATION: Synthetic primer

<400> SEQUENCE: 51
cgagcagaag acgcattgct tcaa                                         24

<210> SEQ ID NO 52
<211> LENGTH: 24
<212> TYPE: DNA
<213> ORGANISM: Artificial Sequence
<220> FEATURE:
<223> OTHER INFORMATION: Synthetic primer

<400> SEQUENCE: 52
cggccttggc tatcatacat caca                                         24

<210> SEQ ID NO 53
<211> LENGTH: 24
<212> TYPE: DNA
<213> ORGANISM: Artificial Sequence
<220> FEATURE:

<223> OTHER INFORMATION: Synthetic primer

<400> SEQUENCE: 53
atttgggacg gcgaacagaa gaca                                              24

<210> SEQ ID NO 54
<211> LENGTH: 24
<212> TYPE: DNA
<213> ORGANISM: Artificial Sequence
<220> FEATURE:
<223> OTHER INFORMATION: Synthetic primer

<400> SEQUENCE: 54
atcctggatg ggcaactcag atgt                                              24

<210> SEQ ID NO 55
<211> LENGTH: 20
<212> TYPE: DNA
<213> ORGANISM: Artificial Sequence
<220> FEATURE:
<223> OTHER INFORMATION: Synthetic primer

<400> SEQUENCE: 55
caatgcgggg aggagaagtc                                                   20

<210> SEQ ID NO 56
<211> LENGTH: 20
<212> TYPE: DNA
<213> ORGANISM: Artificial Sequence
<220> FEATURE:
<223> OTHER INFORMATION: Synthetic primer

<400> SEQUENCE: 56
ctctggacca aactgtggcg                                                   20

<210> SEQ ID NO 57
<211> LENGTH: 18
<212> TYPE: DNA
<213> ORGANISM: Artificial Sequence
<220> FEATURE:
<223> OTHER INFORMATION: Synthetic primer

<400> SEQUENCE: 57
cccccggcgg caatagca                                                     18

<210> SEQ ID NO 58
<211> LENGTH: 20
<212> TYPE: DNA
<213> ORGANISM: Artificial Sequence
<220> FEATURE:
<223> OTHER INFORMATION: Synthetic primer

<400> SEQUENCE: 58
tcggcgccgg ggagatacat                                                   20

<210> SEQ ID NO 59
<211> LENGTH: 20
<212> TYPE: DNA
<213> ORGANISM: Artificial Sequence
<220> FEATURE:
<223> OTHER INFORMATION: Synthetic primer

<400> SEQUENCE: 59
cacgatgccc aaggagatgt                                                   20

```
<210> SEQ ID NO 60
<211> LENGTH: 20
<212> TYPE: DNA
<213> ORGANISM: Artificial Sequence
<220> FEATURE:
<223> OTHER INFORMATION: Synthetic primer

<400> SEQUENCE: 60
ggtggttgca gatgctgttg                                              20
```